(12) United States Patent
O'Dell et al.

(10) Patent No.: US 6,324,298 B1
(45) Date of Patent: Nov. 27, 2001

(54) AUTOMATED WAFER DEFECT INSPECTION SYSTEM AND A PROCESS OF PERFORMING SUCH INSPECTION

(75) Inventors: Jeffrey O'Dell, Bloomington; Mark Harless, New Hope; Thomas Verburgt, Eden Prairie, all of MN (US)

(73) Assignee: August Technology Corp., Bloomington, MN (US)

( * ) Notice: Subject to any disclaimer, the term of this patent is extended or adjusted under 35 U.S.C. 154(b) by 0 days.

(21) Appl. No.: 09/352,564

(22) Filed: Jul. 13, 1999

Related U.S. Application Data

(60) Provisional application No. 60/092,923, filed on Jul. 15, 1998, and provisional application No. 60/092,701, filed on Jul. 14, 1998.

(51) Int. Cl.[7] ........................................... G06K 9/62
(52) U.S. Cl. ............................................... 382/149
(58) Field of Search ..................... 382/145, 148, 382/149, 217, 218, 228; 348/87, 126; 356/237.4, 237.5; 250/559.34, 559.4, 559.41, 559.45, 559.46

(56) References Cited

U.S. PATENT DOCUMENTS

| | | | |
|---|---|---|---|
| 4,328,553 | * 5/1982 | Fredriksen et al. | 364/559 |
| 4,823,394 | * 4/1989 | Berkin et al. | 382/8 |
| 5,091,963 | * 2/1992 | Litt et al. | 382/8 |
| 5,497,381 | * 3/1996 | O'Donoghue et al. | 371/28 |
| 5,640,200 | * 6/1997 | Peng et al. | 382/145 |
| 5,641,960 | * 6/1997 | Okubo et al. | 250/310 |
| 5,787,190 | * 7/1998 | Peng et al. | 382/145 |
| 5,850,466 | * 12/1998 | Schott | 382/141 |
| 5,856,844 | * 1/1999 | Batterman et al. | 348/207 |

* cited by examiner

*Primary Examiner*—Leo Boudreau
*Assistant Examiner*—Brian P. Werner
(74) *Attorney, Agent, or Firm*—John M. Vasuta

(57) ABSTRACT

An automated defect inspection system has been invented and is used on patterned wafers, whole wafers, broken wafers, partial wafers, sawn wafers such as on film frames, JEDEC trays, Auer boats, die in gel or waffle packs, MCMs, etc. and is specifically intended and designed for second optical wafer inspection for such defects as metalization defects (such as scratches, voids, corrosion, and bridging), diffusion defects, passivation layer defects, scribing defects, glassivation defects, chips and cracks from sawing, solder bump defects, and bond pad area defects.

26 Claims, 19 Drawing Sheets

AUTOMATED WAFER DEFECT INSPECTION SYSTEM AND A PROCESS OF PERFORMING SUCH INSPECTION

REFERENCE TO RELATED APPLICATION

This application claims the benefit of U.S. Provisional Application Nos. 60/092,923, file date Jul. 14, 1998 and 60/092,701, filed on Jul. 15, 1998.

BACKGROUND OF THE INVENTION

1. Technical Field

The present invention relates to defect inspection systems for the semiconductor industry. More particularly, the present invention relates to an automated defect inspection system for patterned wafers, whole wafers, sawn wafers such as on film frames, JEDEC trays, Auer boats, die in gel or waffle packs, multi-chip modules often referred to as MCMs, etc. that is specifically intended and designed for second optical wafer inspection for such defects as metalization defects (such as scratches, voids, corrosion, and bridging), diffusion defects, passivation layer defects, scribing defects, glassivation defects, chips and cracks from sawing, and bump or bond pad area defects such as gold or solder bump defects or similar interconnect defects. Specifically, the present invention is an automated defect inspection system for integrated circuits, LCD panels with photolithography circuitry embedded therein, etc. where the system is used as follows: the system is trained by viewing a plurality of known good die under an imaging head resulting in a good die model, an inspection recipe is inputted into the system to define inspection parameters, defect inspection occurs where die are loaded onto, aligned in and viewed by an imaging head for defects in comparison to the good die model, an optional review of the identified defects may occur, and the user may optionally receive or export a report thereon.

2. Background Information

Over the past several decades, the semiconductor has exponentially grown in use and popularity. The semiconductor has in effect revolutionized society by introducing computers, electronic advances, and generally revolutionizing many previously difficult, expensive and/or time consuming mechanical processes into simplistic and quick electronic processes. This boom in semiconductors has been fueled by an insatiable desire by business and individuals for computers and electronics, and more particularly, faster, more advanced computers and electronics whether it be on an assembly line, on test equipment in a lab, on the personal computer at one's desk, or in the home electronics and toys.

The manufacturers of semiconductors have made vast improvements in end product quality, speed and performance as well as in manufacturing process quality, speed and performance. However, there continues to be demand for faster, more reliable and higher performing semiconductors.

One process that has evolved over the past decade or so is the semiconductor inspection process. The merit in inspecting semiconductors throughout the manufacturing process is obvious in that bad wafers may be removed at the various steps rather than processed to completion only to find out a defect exists either by end inspection or by failure during use.

A typical example of the semiconductor manufacture process is summarized as follows. Bare whole wafers are manufactured. Thereafter, circuitry is created on the bare whole wafers. The whole wafer with circuitry is then sawn into smaller pieces known in the industry as die. Thereafter, the die are processed, as is well known in the art, typically as die in waffle and/or gel packs or on substrates.

Today, it is well known that various inspection processes occur during this semiconductor process. Bare wafer inspection may occur on bare whole wafers not long after initial creation from sand and/or after polishing of the wafer but always prior to the deposit of any layers that form the circuitry. Defects being inspected for during bare wafer inspection include surface particulates and surface imperfections or irregularities.

During the deposition of layers, that is the circuit building, on the whole wafer, one or more first optical inspections may occur. First ($1^{st}$) optical inspection is "in process" inspection of wafers during circuitry creation. This $1^{st}$ inspection may be after each layer is deposited, at certain less often intervals, or only once during or after all deposits. This $1^{st}$ optical inspection is usually a sub-micron level inspection in the range of 0.1 micron to <1 micron. This process is used to check for mask alignment or defects such as extra metal, missing metal, contaminants, etc. This $1^{st}$ inspection occurs during circuitry development on the wafer.

Once the whole wafers are at least fully deposited on, that is all of the circuitry is created thereon, a post $1^{st}$ (or 1.5) inspection occurs on the fully processed whole wafers. Generally, this is prior to the deposit of a passivation layer although it need not be. In addition, this post 1st inspection is generally prior to electrical testing or probing of the whole wafers. This inspection is typically a 0.5 micron to 1 micron optical inspection.

After the whole wafers are fully processed, one or more $2^{nd}$ optical inspections are performed. Front end $2^{nd}$ optical inspections occur after the whole wafers are fully processed and, if probing is necessary, just before or right after this probing or electrical testing to determine the quality of the devices. Back end $2^{nd}$ optical inspections occur at various stages such as during the applying of bumps to the die or wafer, during or after sawing of the wafers into sawn wafers, during or after dicing of the wafers, during or after picking up and placing of the die onto other packages such as trays or waffle or gel packs, during or after placing of the wafers onto a substrate, etc. This $2^{nd}$ optical inspection is generally at a 1+ micron level and is generally looking for defects such as metalization defects (such as scratches, voids, corrosion, and bridging), diffusion defects, passivation layer defects, scribing defects, glassivation defects, chips and cracks from sawing, and probe or bond pad area defects.

After actual packaging, $3^{rd}$ optical inspections occur. This packaging involves at least one of the following: placing the die on a substrate, wire bonding the die, connecting the leads, attaching the balls to a flip chip, etc. At this point, the inspection involves inspecting the ball grid array, lead straightness, wire bonding, ink marking, and for any package defects such as chips, cracks and voids. This $3^{rd}$ level inspection is generally at a 5+ micron level.

The focus of the semiconductor inspection industry has been bare wafer and 1st optical inspection. Numerous market leaders have developed, patented, and are manufacturing and marketing $1^{st}$ optical inspection systems to perform these inspections including ADE, KLA, Tencor, Inspex, Applied, Orbit and others.

Often this equipment is very expensive and large. At the $1^{st}$ inspection stage, this expense and machine size issue is not as significant as at later inspection stages because only a relatively few parties manufacture the silicon wafers and thus need to inspect bare wafers in comparison to the vast number of companies that buy bare or sawn wafers and further process them into finished chips. These often expensive and large inspection devices are not cost justifiable for smaller shops and as such, inspection equipment is needed that satisfies this need at the $2^{nd}$ and $3^{rd}$ stages as well as is more economical for the vast many smaller companies that finish process wafers.

To a lesser extent, some resources have been spent on $3^{rd}$ optical inspection and several companies including STI, View Engineering, RVSI, and ICOS have developed systems for this purpose and are marketing those systems.

However, none of these systems address the particular and unique constraints of $2^{nd}$ optical and this area has been largely ignored. In actual application, $2^{nd}$ optical inspection has been marginally performed by manual inspection using humans and microscopic equipment. This manual process is inaccurate due to various factors including stress, eye fatigue and boredom of the operator as well as different perceptions by different operators as to the significance of a finding. In addition, smaller circuit geometry and higher throughput requirements are increasing the demands on semiconductor inspection at this $2^{nd}$ optical level, all of which further results in operator stress, eye fatigue, and sometimes lower quality.

In addition at the $2^{nd}$ optical inspection stage to the need for inspecting for metalization defects (such as scratches, voids, corrosion, and bridging), diffusion defects, passivation layer defects, scribing defects, glassivation defects, chips and cracks from sawing, etc., bumps have taken on additional importance of recent. This is due to the recent surge in the use of bump interface connects, or flip chips, rather than leads which has magnified the importance of $2^{nd}$ optical inspection and thus the need for equipment and systems over manual inspection.

OBJECTIVES AND SUMMARY OF THE INVENTION

It is an objective of the present invention to provide an automated inspection system that replaces the current manual inspection process.

It is a further objective of the present invention to provide a new, state of the art $2^{nd}$ optical inspection system.

It is further an objective of the present invention to provide an automated defect inspection system of patterned wafers, whole wafers, sawn wafers, JEDEC trays, Auer boats, die in gel or waffle packs, MCMs, etc.

It is further an objective of the present invention to provide an automated defect inspection system that is specifically intended and designed for second optical wafer inspection It is further an objective of the present invention to provide an automated defect inspection system for inspecting for defects such as metalization defects (such as scratches, voids, corrosion, and bridging), diffusion defects, passivation layer defects, scribing defects, glassivation defects, chips and cracks from sawing, probe area defects, bump area defects and/or bond pad area defects.

It is further an objective of the present invention to provide an automated defect inspection system that eliminates or significantly reduces the need for manual microscopic inspecting of every die in every wafer.

It is further an objective of the present invention to provide an automated defect inspection system that views the ever-smaller circuit geometry in an accurate and rapid manner.

It is further an objective of the present invention to provide an automated defect inspection system that provides for higher throughput than manual inspection.

It is further an objective of the present invention to provide an automated defect inspection system that provides for improved inspection quality and consistency.

It is further an objective of the present invention to provide an automated defect inspection system that provides for improved process control.

It is further an objective of the present invention to provide an automated defect inspection system that has inspection recipes therein and can create, copy and edit such recipes to customize the system to the user's inspection requirements.

It is further an objective of the present invention to provide an automated defect inspection system that uses digital image analysis to perform semiconductor wafer inspection.

It is further an objective of the present invention to provide an automated defect inspection system that is trained by inspecting good die so that once trained the system detects variations from what it has learned.

It is further an objective of the present invention to provide an automated defect inspection system that is trainable.

It is further an objective of the present invention to provide an automated defect inspection system that develops a model of a good die and uses this model to inspect unknown quality die.

It is further an objective of the present invention to provide an automated defect inspection system that includes a "good die" training step and a defect inspection step using the good die model.

It is further an objective of the present invention to provide an automated defect inspection system that includes a "good die" training step, an inspection recipe creation step and a defect inspection step.

It is further an objective of the present invention to provide an automated defect inspection system that includes a "good die" training step, an inspection recipe creation step, a defect inspection step, a defect review step, and a report issuing or exporting step.

It is further an objective of the present invention to provide an automated defect inspection system that provides for multi-dimensional alignment of each wafer, substrate or other device having die thereon to be inspected such that every die is uniformly positioned.

It is further an objective of the present invention to provide an automated defect inspection system that provides for x, y and theta ($\theta$) alignment of each wafer, substrate or other device having die thereon to be inspected such that every die is uniformly positioned.

It is further an objective of the present invention to provide an automated defect inspection system that provides for course alignment, fine alignment, and/or focusing of each wafer.

It is further an objective of the present invention to provide an automated defect inspection system that provides "good die" modeling by viewing multiple good dies and developing a model therefrom.

It is further an objective of the present invention to provide an automated defect inspection system that provides for defect inspection using an imaging head or camera to view static and properly aligned die.

It is further an objective of the present invention to provide an automated defect inspection system that provides for defect inspection using an imaging head or camera to view dynamic or moving yet properly aligned die.

It is further an objective of the present invention to provide an automated defect inspection system that provides for defect inspection using an imaging head or camera to view dynamic or moving yet properly aligned die where a strobe illumination is used to capture still views of the dynamically moving die.

It is further an objective of the present invention to provide an automated defect inspection system that provides for review of the system detected defects whereby the user need not look at all die or all parts of die and instead only views the marked or noted defects.

It is further an objective of the present invention to provide an automated defect inspection system that provides means for accounting for drifting or non-regularity of die positioning or spacing.

It is further an objective of the present invention to provide an automated defect inspection system that provides means to inspect die on a stretched film frame where the dies are irregularly spaced, rotated, drifted, etc.

It is further an objective of the present invention to provide an automated defect inspection system that provides a method to measure the size, position, shape, geometry, and other characteristics of solder bumps, gold bumps, bond pads or the like.

It is further an objective of the present invention to provide an automated defect inspection system that provides a method to inspect the quality of gold bumps, solder bumps, interconnects or the like, or the probe marks on bond pads.

It is further an objective of the present invention to provide an automated defect inspection system that provides a method to detect defects on bond pads, bumps or interconnects.

Still other advantages and benefits of the invention will become apparent to those skilled in the art upon a reading and understanding of the following summary and detailed description.

Accordingly, the present invention satisfies these and other objectives as it relates to automated inspection equipment, systems and processes. Specifically, the present invention is an automated method of inspecting a semiconductor wafer in any form including whole patterned wafers, sawn wafers, broken wafers, partial wafers, and wafers of any kind on film frames, dies, die in gel paks, die in waffle paks, multi-chip modules often called MCMs, JEDEC trays, Auer boats, and other wafer and die package configurations for defects, the method comprising (1) training a model as to parameters of a good wafer via optical viewing of multiple known good wafers, and (2) inspecting unknown quality wafers using the model.

BRIEF DESCRIPTION OF THE DRAWINGS

Preferred embodiment of the invention, illustrative of the best mode in which applicant has contemplated applying the principles, are set forth in the following description and are shown in the drawings and are particularly and distinctly pointed out and set forth in the appended claims.

Similar numerals refer to similar parts throughout the drawings.

DESCRIPTION OF THE PREFERRED EMBODIMENT

Figure 1:
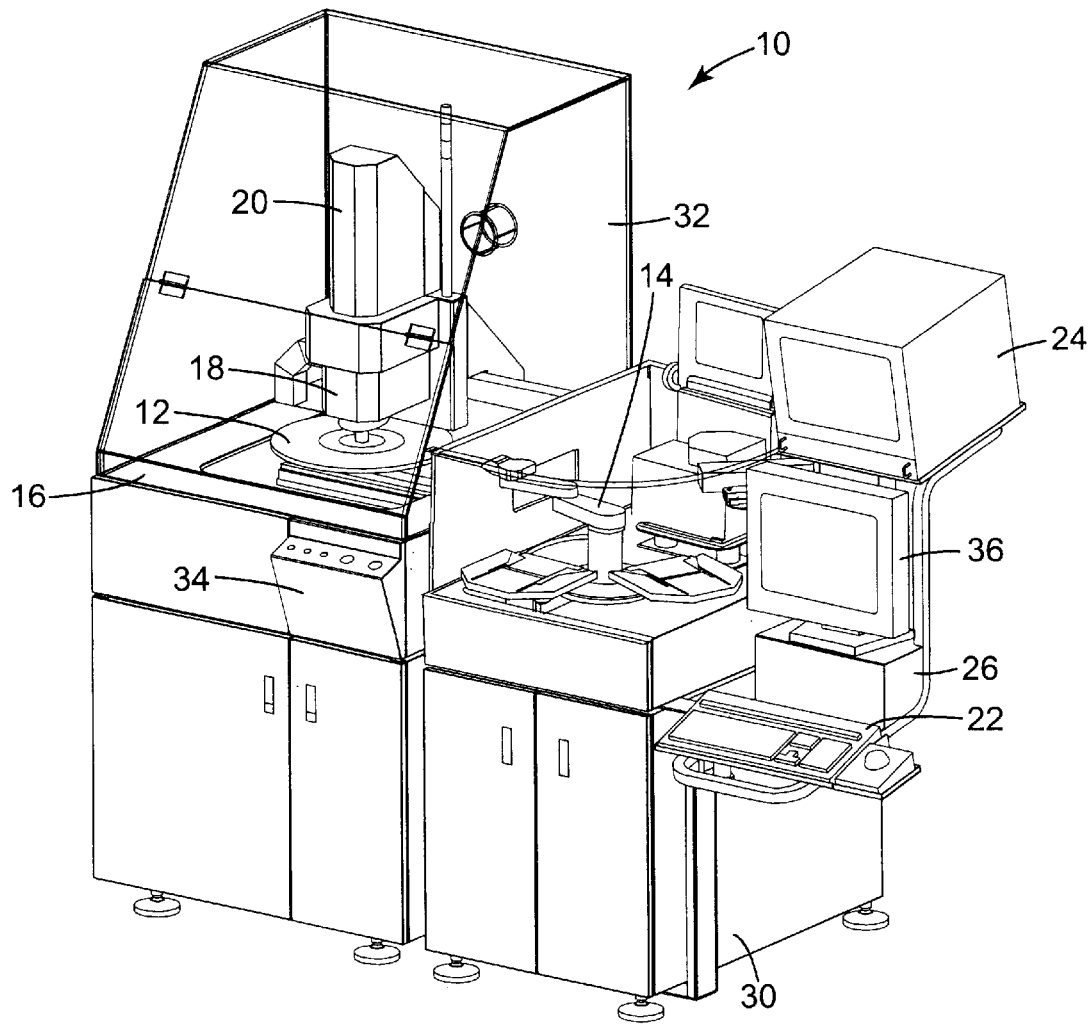
FIG. 1 is a perspective view of one embodiment of the system.
Figure 8:
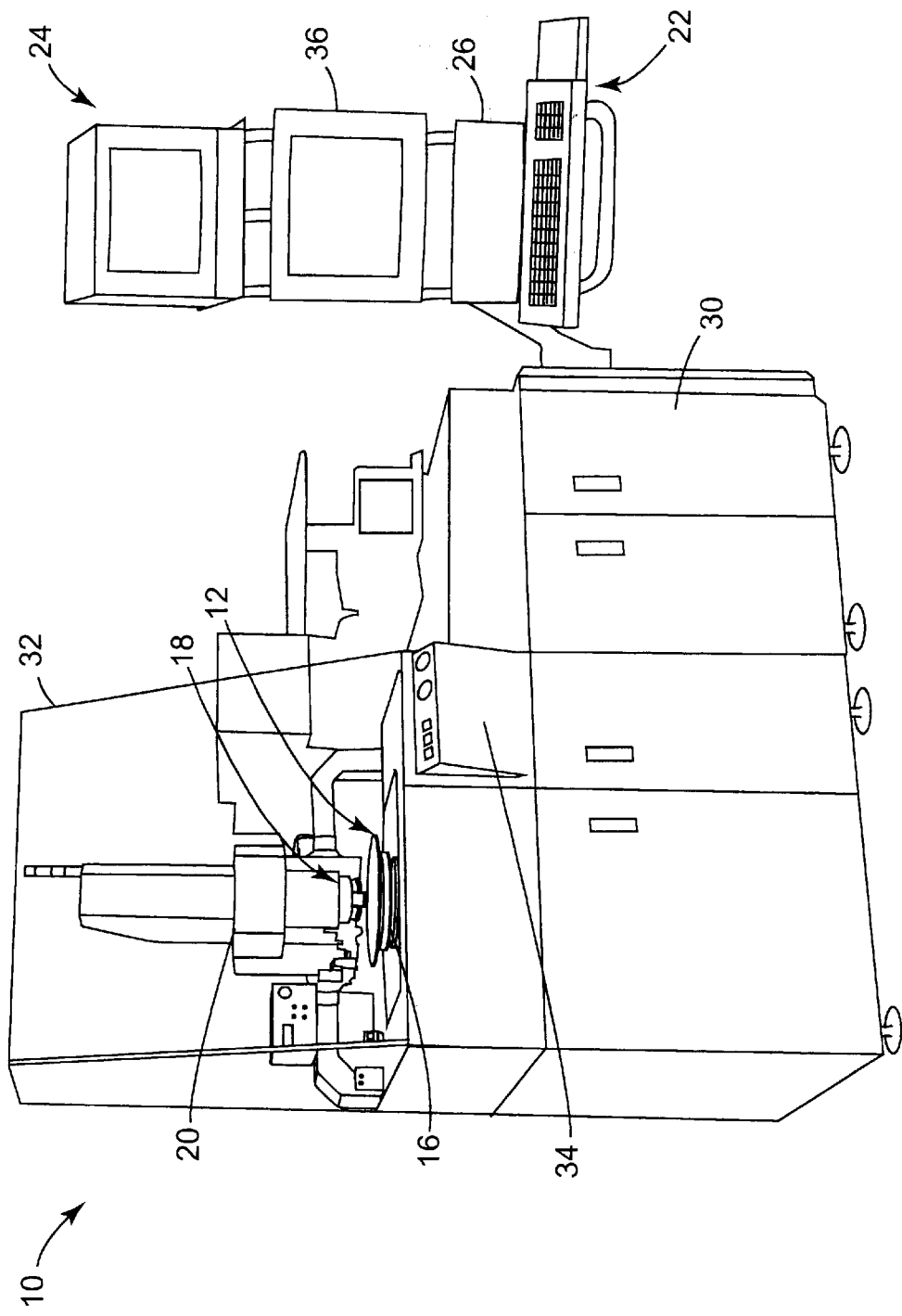
FIG. 8 is an overall perspective view of a similar system to that shown in FIG. 1 taken at a different angle.
Figure 9:
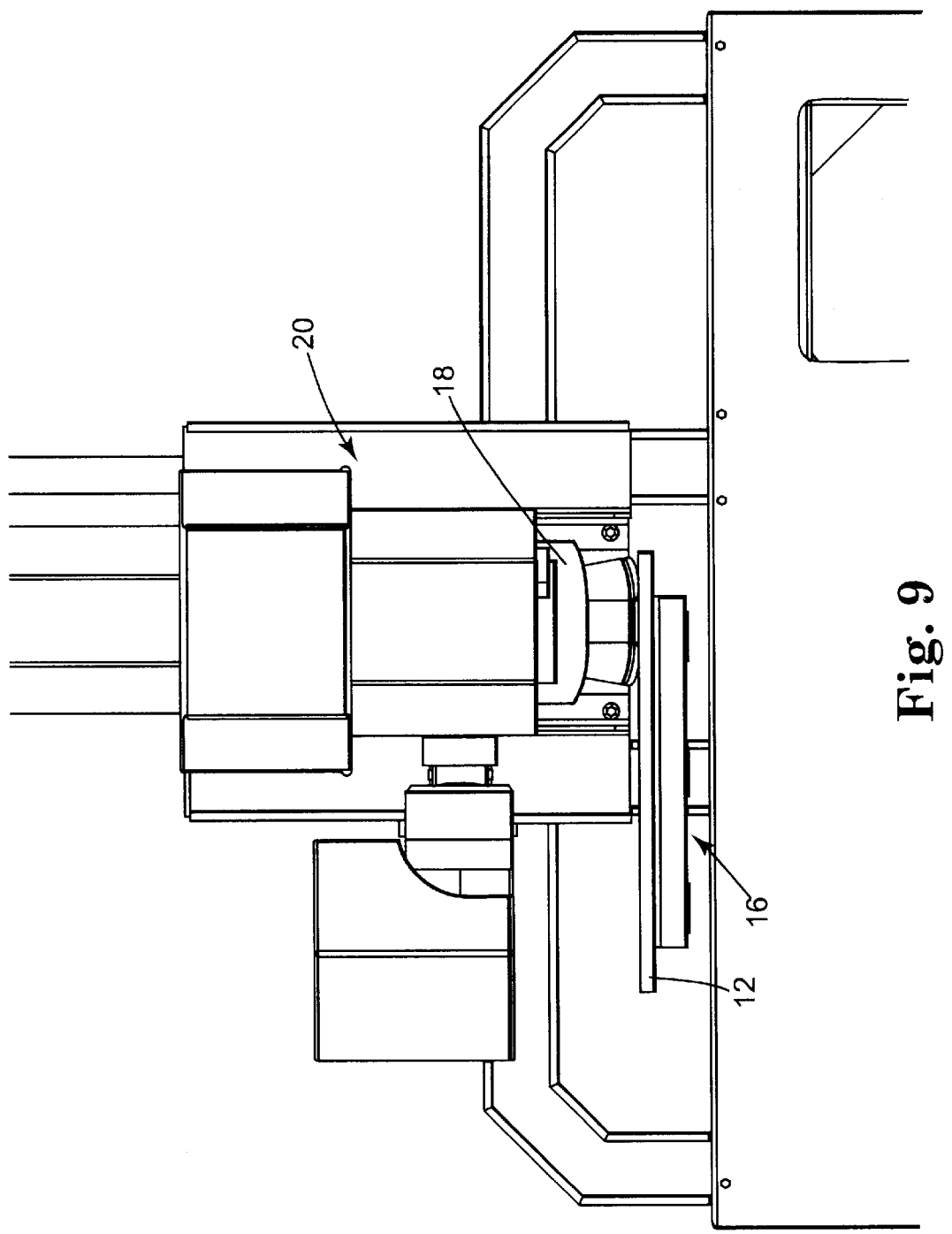
FIG. 9 is a front view of the wafer top plate and optics.
Figure 10:
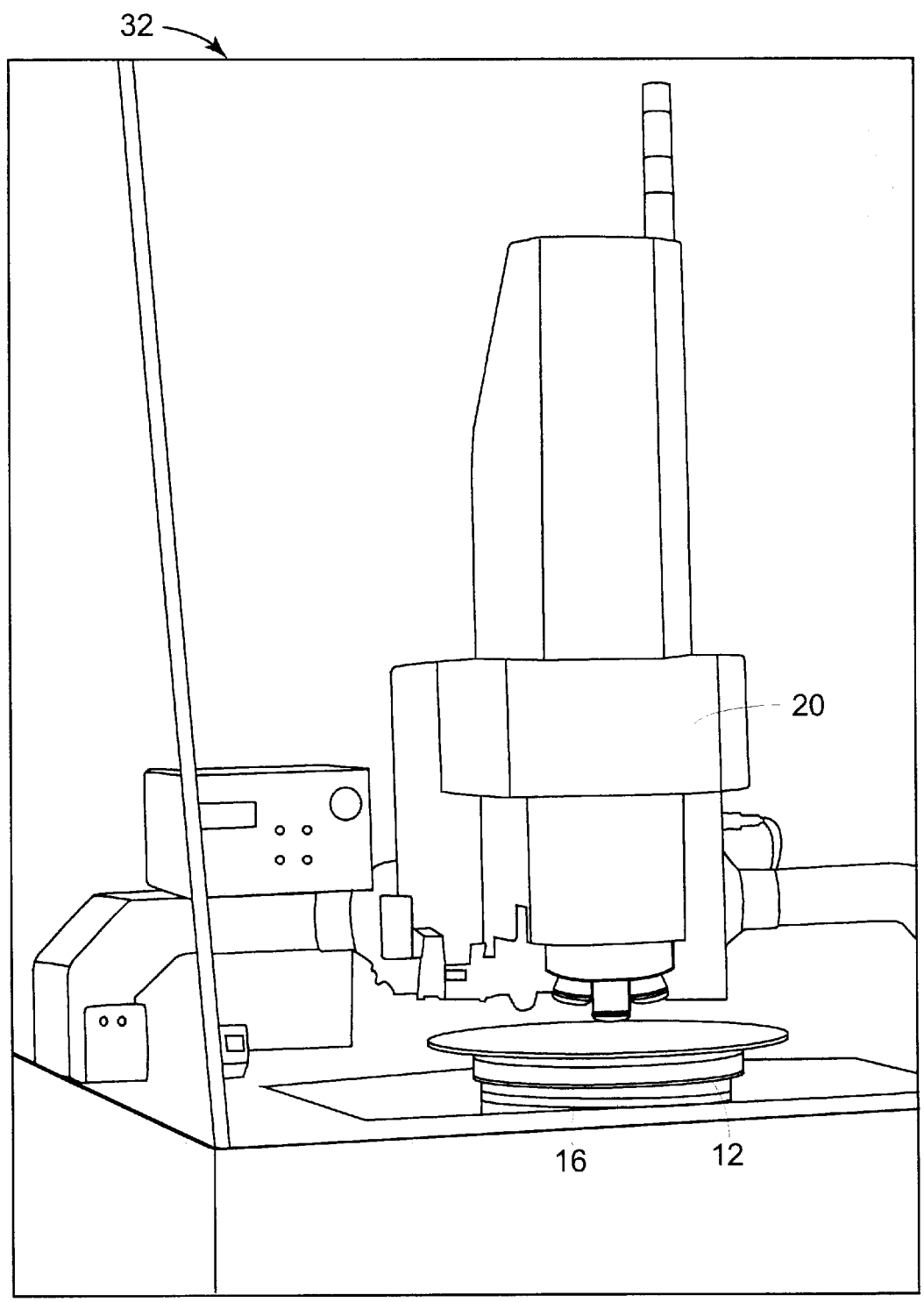
FIG. 10 is a left front perspective view of a portion of the inspection station including the wafer top plate and optics.
Figure 11:
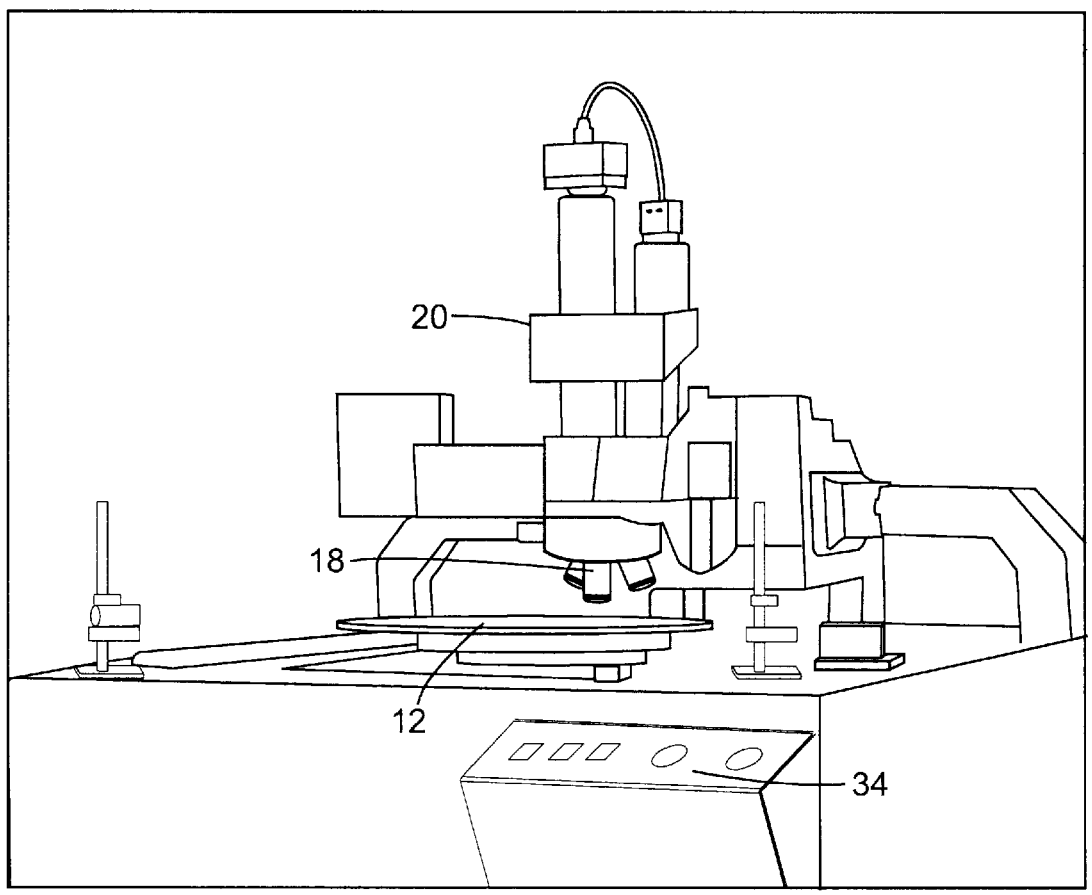
FIG. 11 is a right front perspective view of the top portion of the inspection station.
Figure 12:
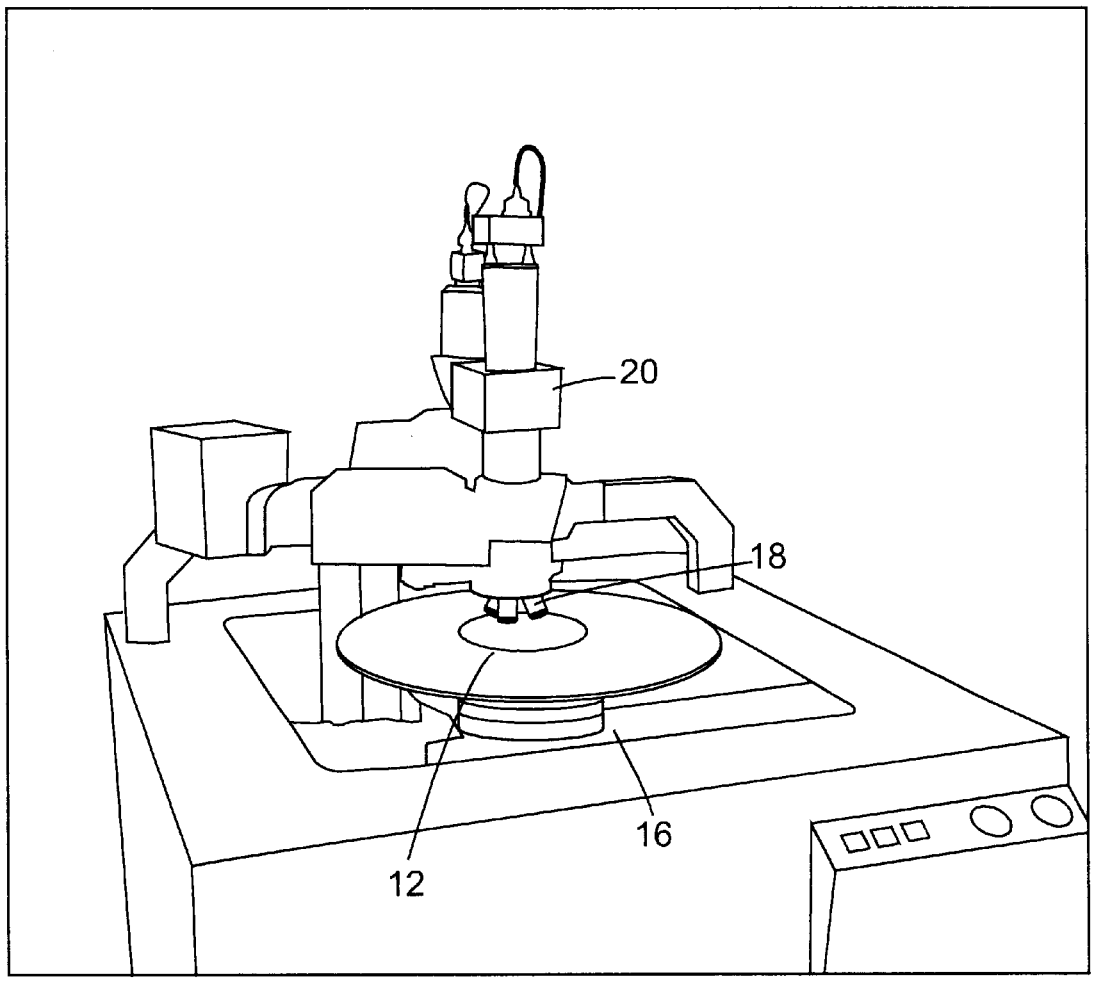
FIG. 12 is a right side perspective view of the top portion of the inspection station as shown in FIG. 11.
Figure 13:
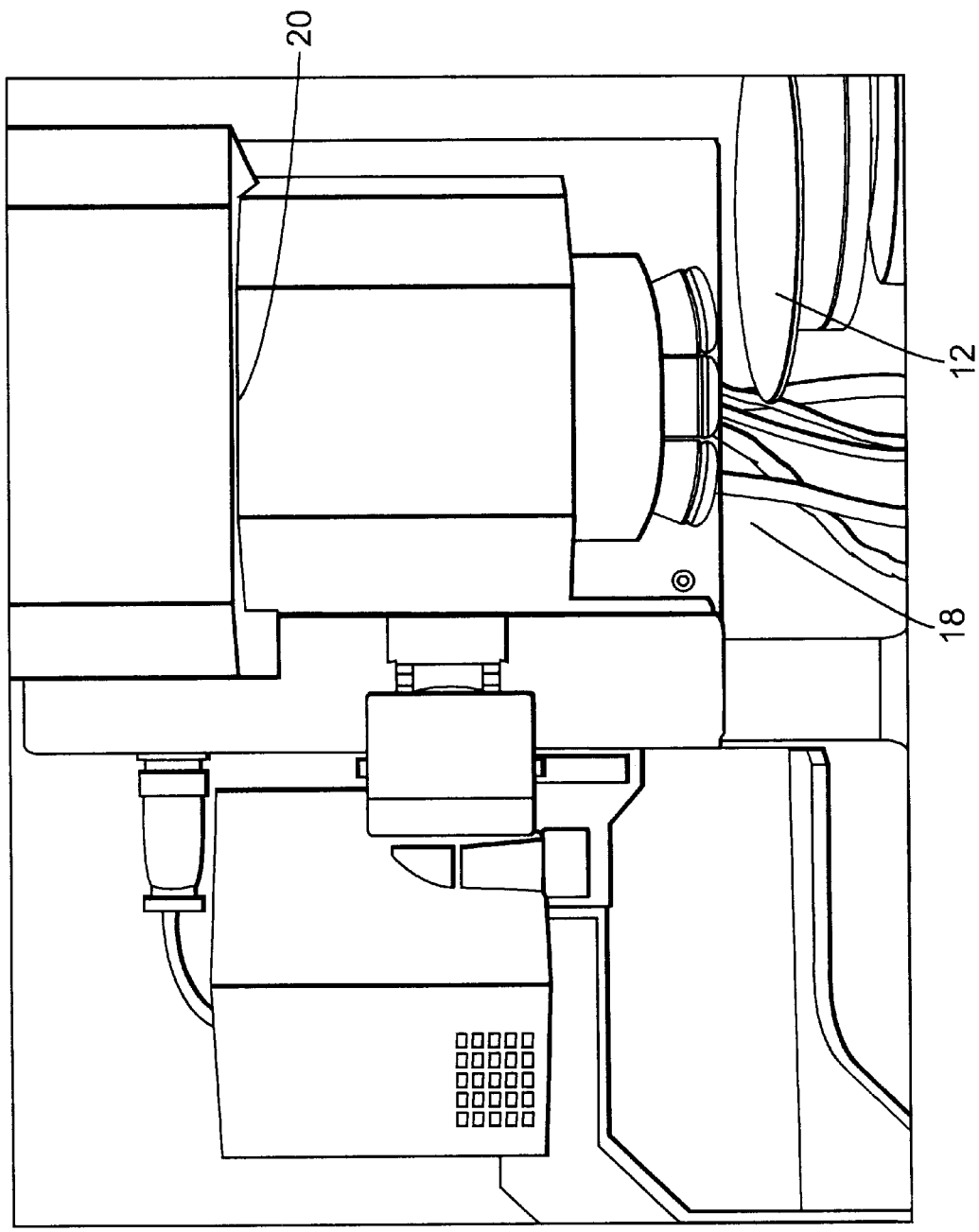
FIG. 13 is an enlarged view of the optics and wafer top plate.
Figure 14:
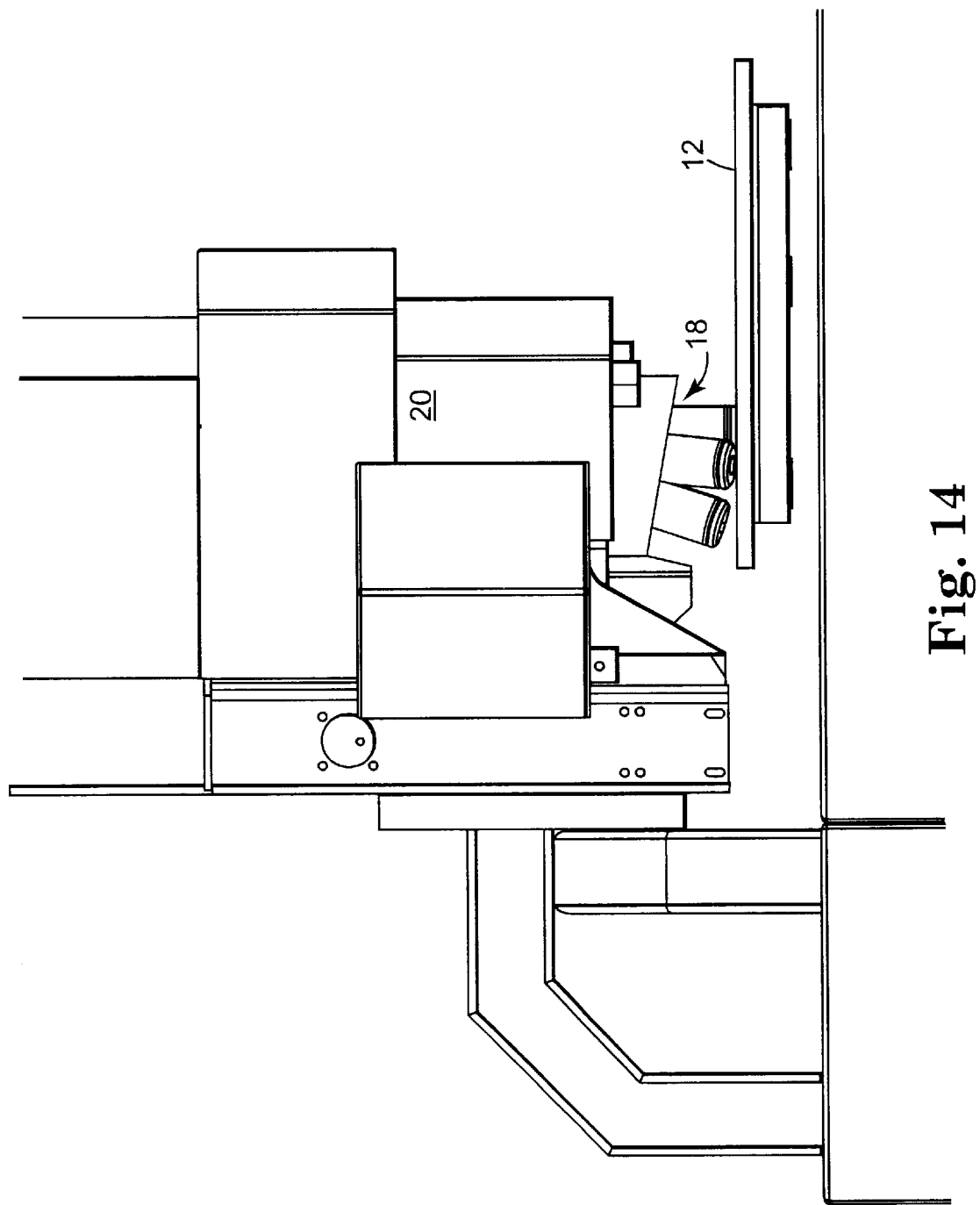
FIG. 14 is a side view of the wafer top plate and optics of FIG. 9.
Figure 15:
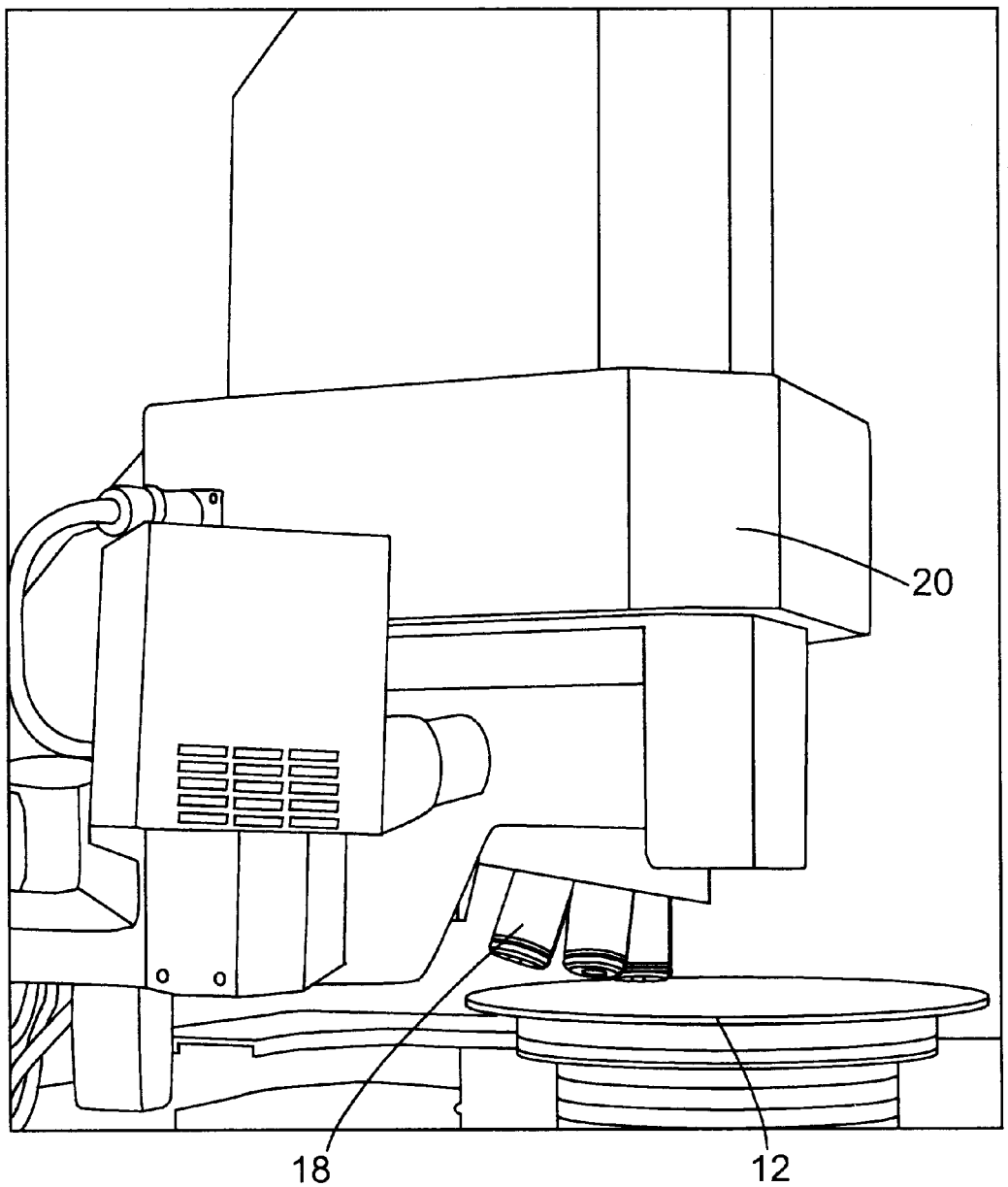
FIG. 15 is a left side perspective view of the top portion of the inspection station as shown in FIGS. 10–12.
Figure 16:
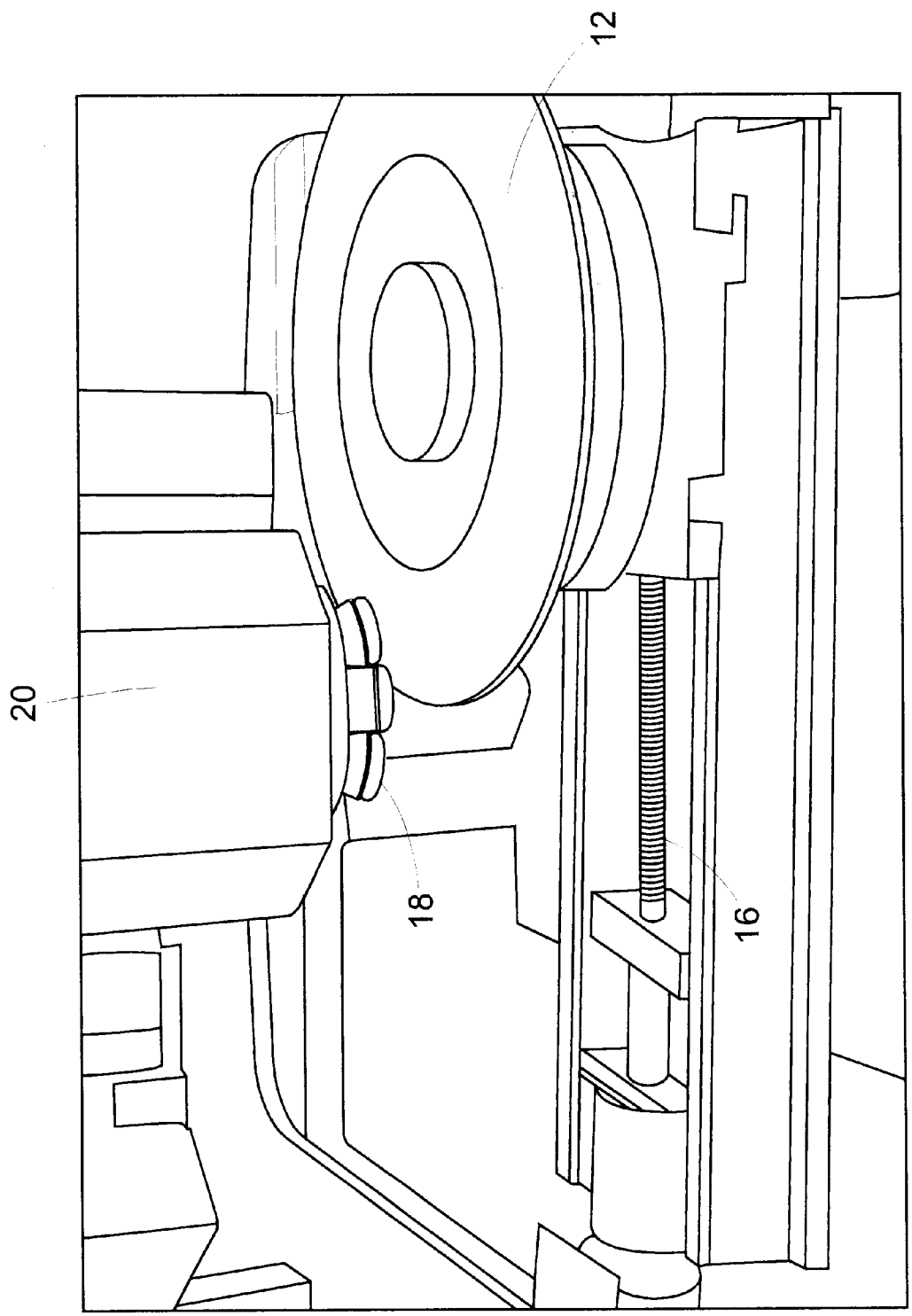
FIG. 16 is an enlarged view of the wafer top plate and the x, y and θ aligner.
Figure 17:
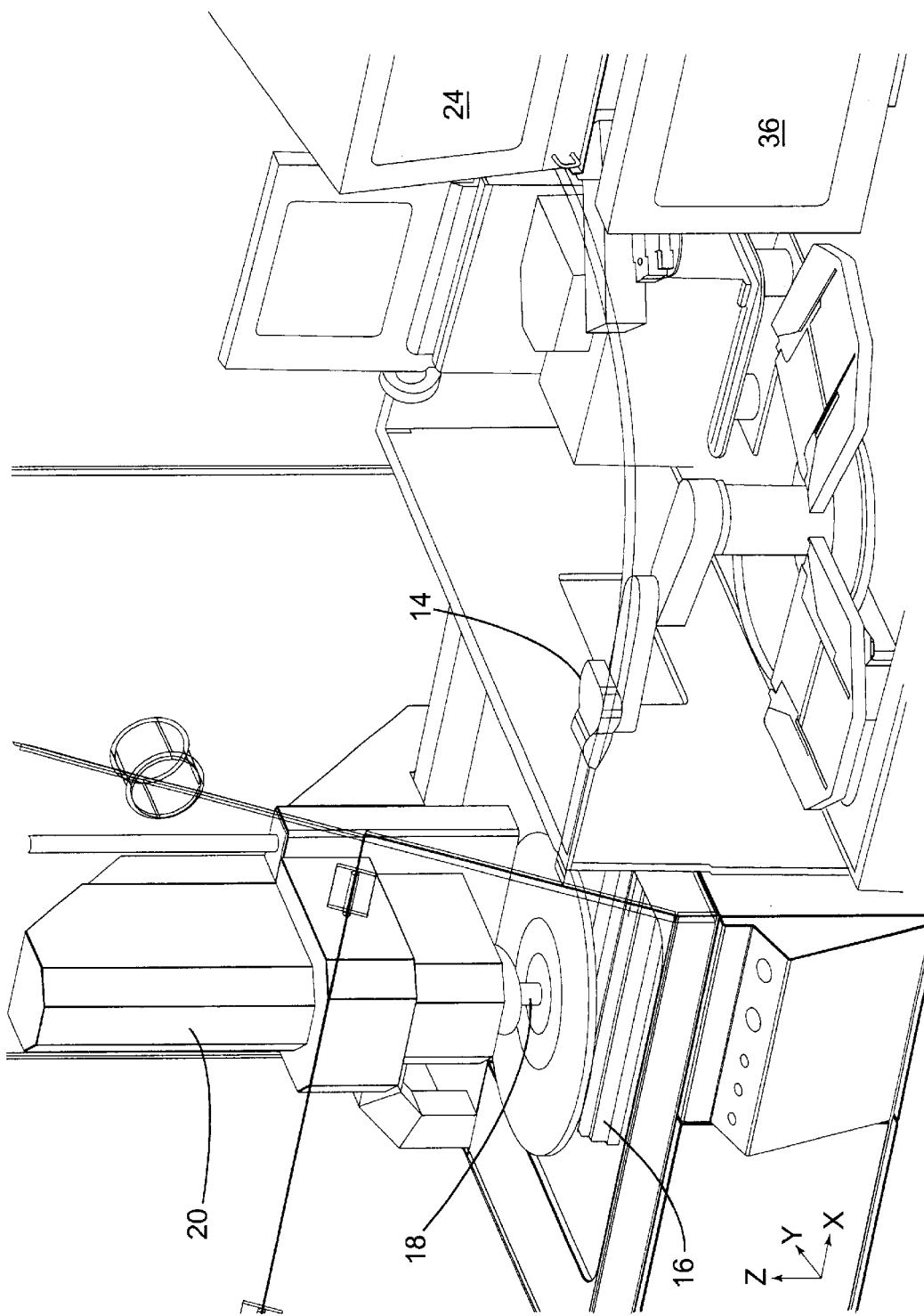
FIG. 17 is a partial perspective view of the top portions of the inspection and wafer handling stations.
Figure 18:
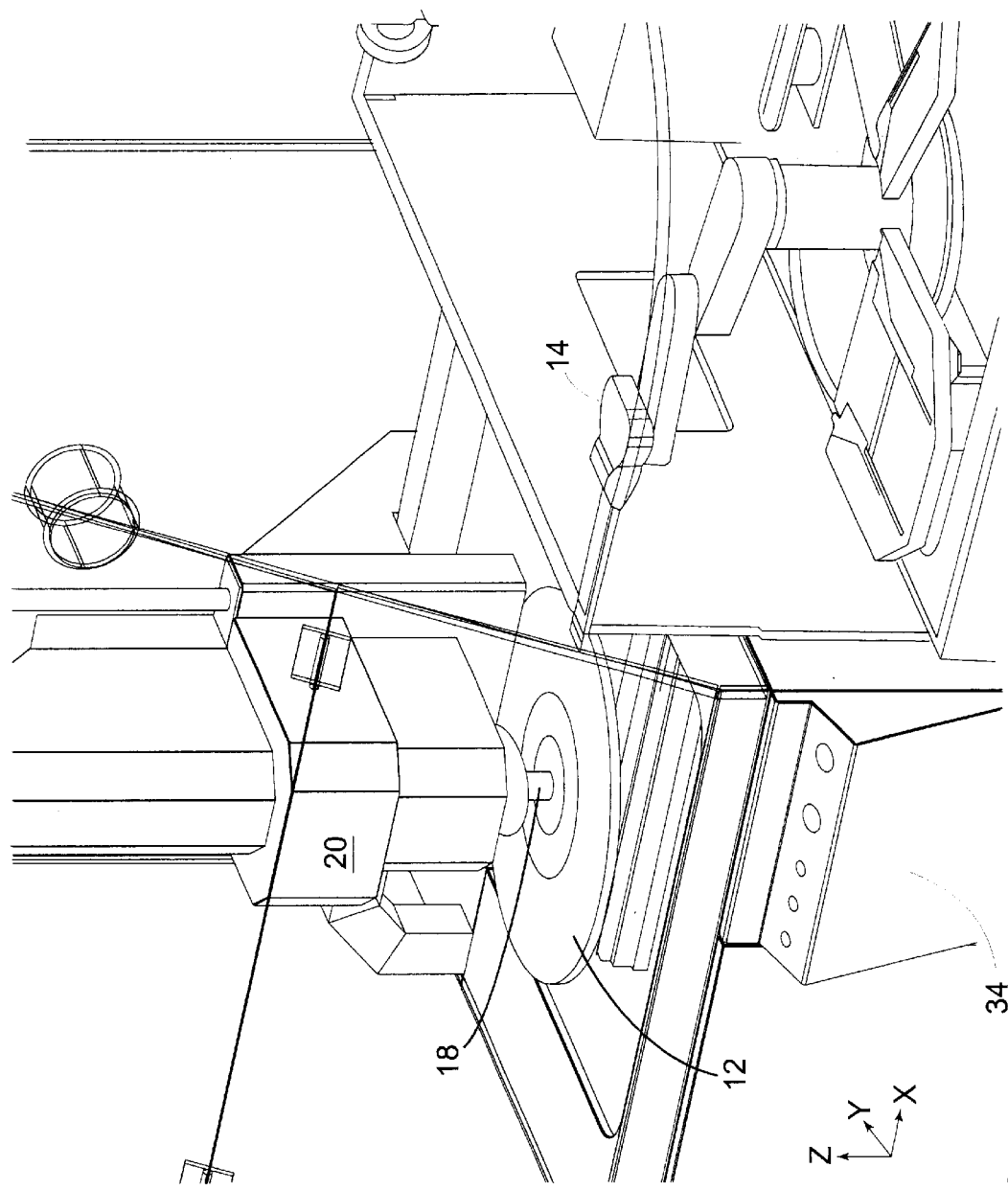
FIG. 18 is an enlarged view of the wafer handling and wafer top plate portions of the invention.
Figure 19:
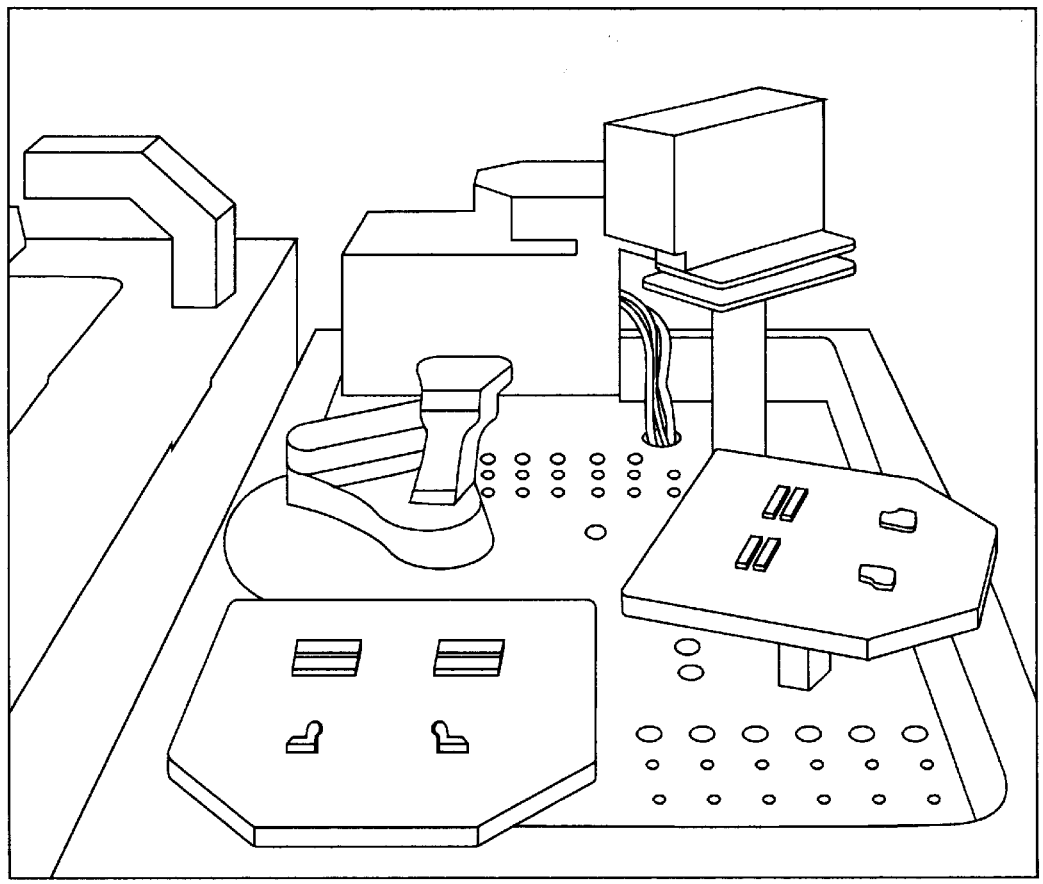
FIG. 19 is a side view of the wafer handling station.

The automated defect inspection system of the present invention is indicated generally at 10 as is best shown overall in FIGS. 1 and 8 (but in detailed portions in FIGS. 2–7 and 9–21) and is used in one environment to find defects on die on patterned wafers W but is intended for this and other uses including for inspecting whole wafers, sawn wafers, broken wafers, wafers of any kind on film frames, die in gel paks, die in waffle paks, MCMs, JEDEC trays, Auer boats, and other wafer and die package configurations (although hereinafter all of these uses shall be referred to generally as inspection of wafers W). The system inspects for many types of defects including, but not limited to, the following: metalization defects (such as scratches, voids, corrosion, bridging, etc.), diffusion defects, passivation layer defects, scribing defects, glassivation defects, chips and cracks from sawing, probe or bond area defects (such as missing probe marks, discoloration, missing metal and probe bridging), diffusion faults, vapox, etc. The system may also be additionally or alternatively used to inspect interconnects or bumps, such as gold or solder bumps, for defects or other characteristics such as size and shape.

Figure 2:
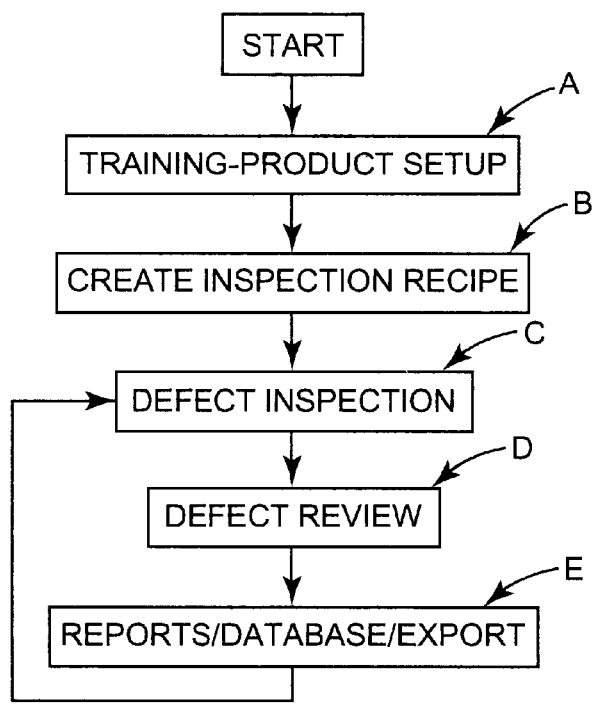
FIG. 2 is an overall flow chart of the process.
Figure 3:
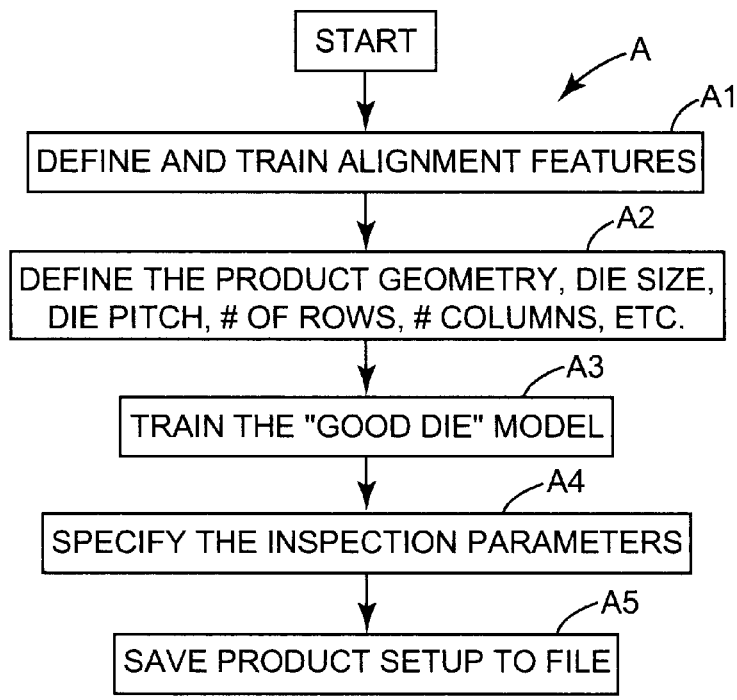
FIG. 3 is a more detailed flow chart of one step in the process as shown in FIG. 2.
Figure 4:
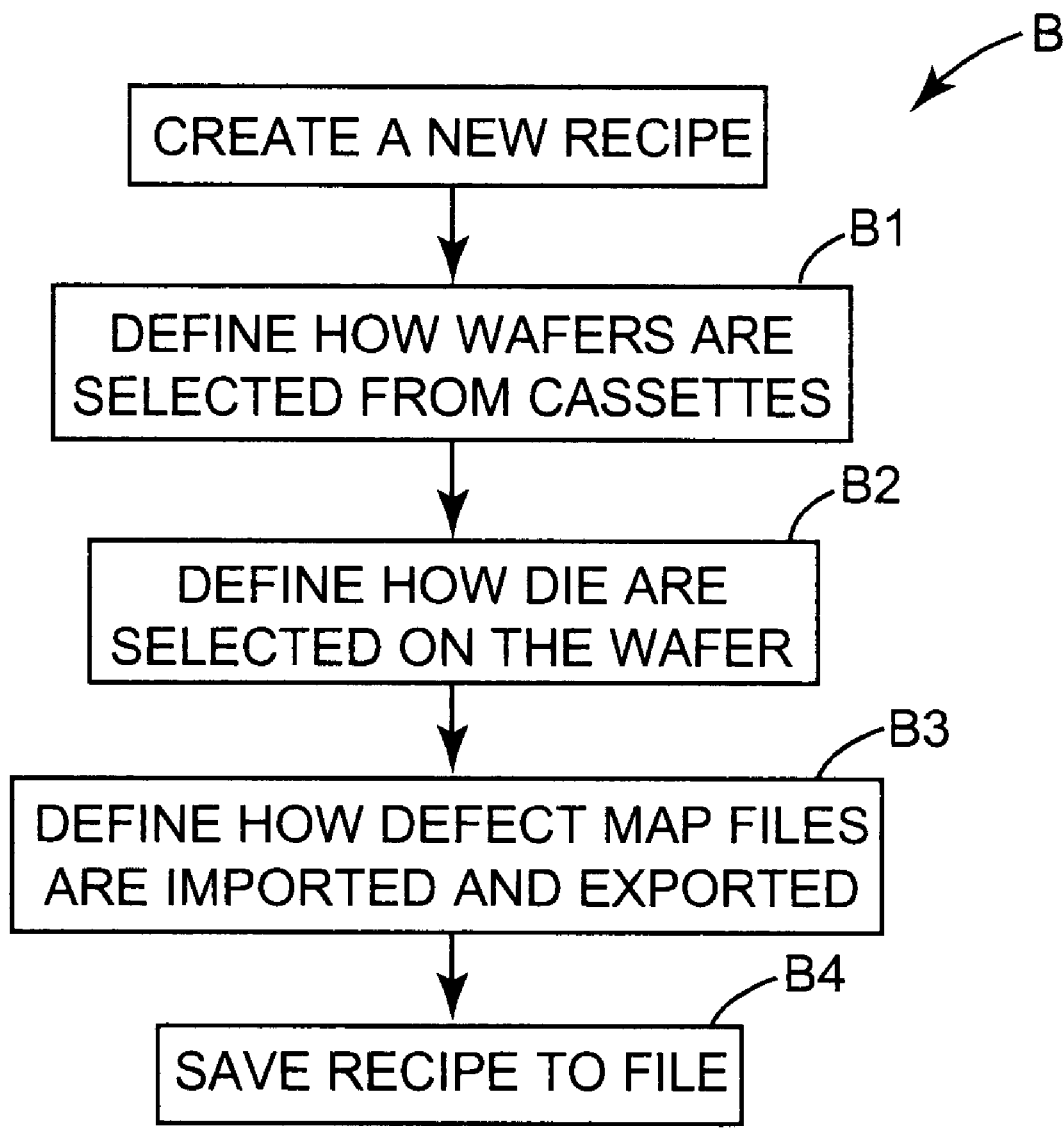
FIG. 4 is a more detailed flow chart of one step in the process as shown in FIG. 2.
Figure 5:
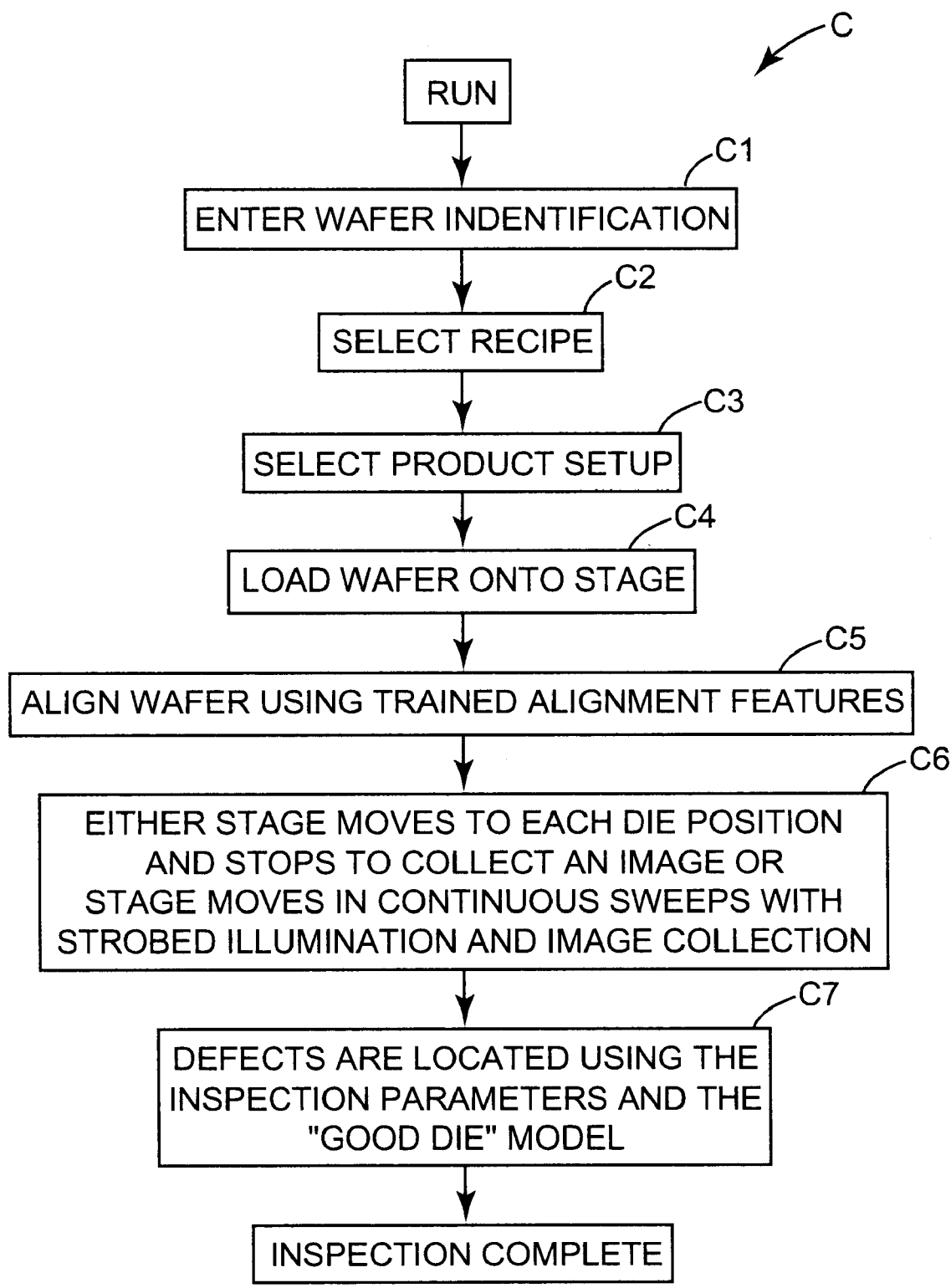
FIG. 5 is a more detailed flow chart of one step in the process as shown in FIG. 2.
Figure 6:
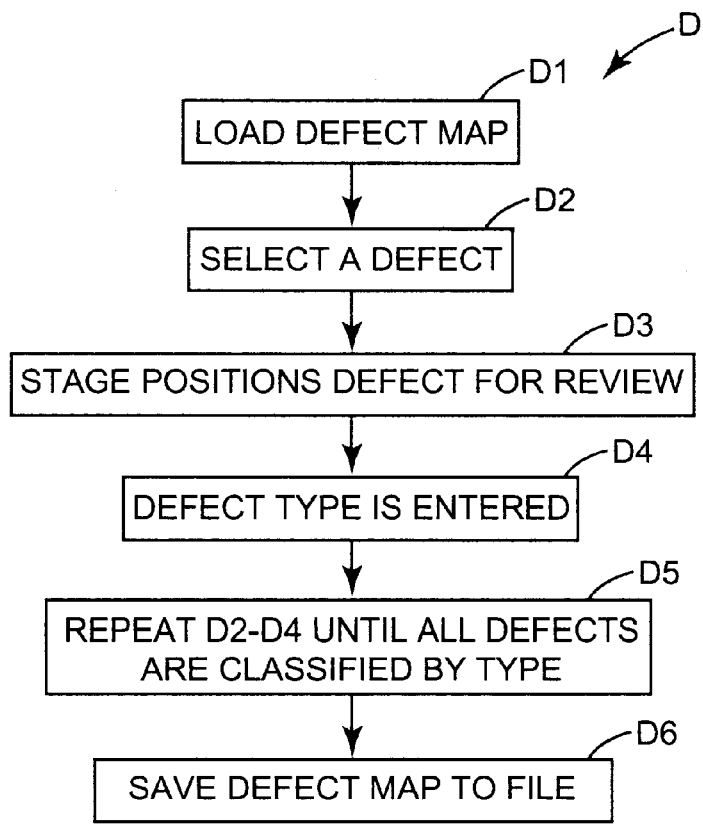
FIG. 6 is a more detailed flow chart of one step in the process as shown in FIG. 2.
Figure 7:
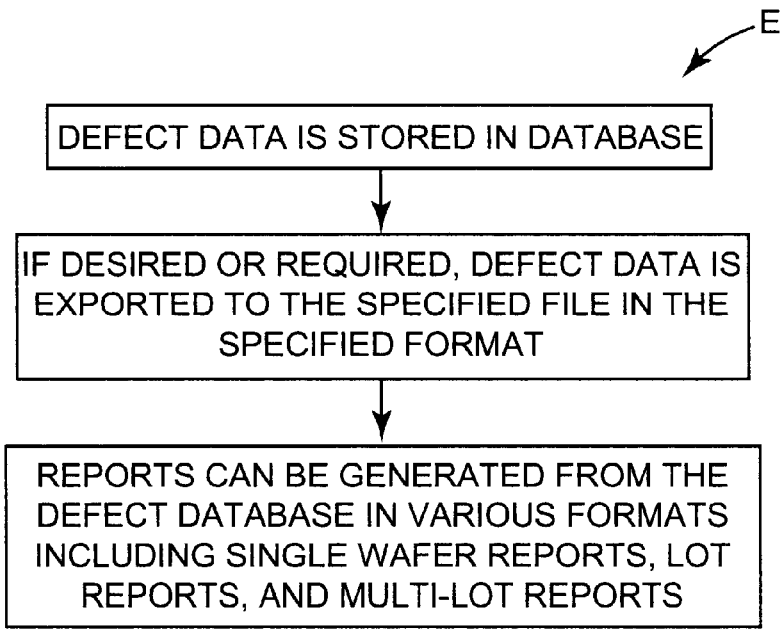
FIG. 7 is a more detailed flow chart of one step in the process as shown in FIG. 2.

The system and process encompasses, in general, a multiple step process as shown in FIG. 2 of training (step A) the system, creating (step B) an inspection recipe, inspecting (step C) die or wafers based upon this training and recipe, defect review (step D) if desired, and defect reporting (step E) if desired. The system 10 for performing this process includes, in general, a wafer test plate 12, means for providing a wafer to the test plate referred to as 14, a wafer alignment device 16 (x-y-θ or x-y-z-θ aligner) for aligning each and every wafer at the same x, y, and θ location or x, y, z, and θ location, a focusing mechanism 18, a camera 20 or other visual inspection device for visual inputting of good die during training and for visual inspection of other unknown quality die during inspection, a parameter input device 22 for inputting parameters and other constraints or information such as sensitivity parameters, geometries, die size, die shape, die pitch, number of rows, number of columns, etc., a display 24 for displaying the view being seen by the camera presently or at any previous saved period, a computer system 26 or other computer-like device having processing and memory capabilities for saving the inputted good die, developing a model therefrom, and comparing or analyzing other die in comparison to the model, a marking head 28, a frame 30, a hood 32, a control panel 34, and a system parameters display 36.

In more detail the system 10 and associated process are as follows. Training (step A) as initially displayed in FIG. 2 and shown in more detail in FIG. 3 involves (1) defining and/or training alignment features and parameters (and storing) in the computer system 26 for use during training where all of this is shown as step A1, (2) defining (and inputting into the computer system) the wafer and/or die geometries, the wafer and/or die sizes, the die pitch, the number of rows, the number of columns, etc. and storing all such information in the computer system 26 for use during training and/or inspecting where all of this is shown as step A2, (3) training the system as to what a "good die" comprises by aligning via device 16 and viewing via camera 20 a plurality of known good die and forming a model within computer system 26 to define what an ideal die should look like based upon the common characteristics viewed where all of this is shown as step A3, (4) setting inspection parameters which are values that indicate to the computer system 26 how close an unknown quality die must match the good die model to be considered a good die (that is, what differences from the exact model are tolerable to still be considered a good die) where all of this is shown as step A4, and (5) saving this training model and its features, parameters, etc. to the computer system 26 as shown by step A5.

Creating (step B) an inspection recipe involves creating a new recipe (if a previously defined recipe is to be used, then the creating step of B is skipped). Creating a new recipe involves (1) defining how wafers W are selected from cassettes or other storage receptacles where all of this is shown as step B1, (2) defining how the dies on each wafer W are to be selected for defect inspection where all of this is shown as step B2 (often dies are merely inspected in sequential or similar order; however, any other order may be defined), (3) defining how defect inspection map files are imported and exported where this is shown as step B3, and (4) save this recipe where this is step B4.

Inspecting (step C), referred to as defect inspection, involves (1) inputting a wafer identification code, if desired, and is referred to as step C1, (2) selecting a recipe that was defined in step B where this selecting is step C2, (3) selecting and inputting a product setup which is step C3, (4) loading a wafer onto the wafer test plate 12 using the wafer providing means 14 where loading is step C4, (5) aligning the wafer on the wafer test plate 12 using the wafer alignment device 16 for aligning each and every wafer at the same x, y, and θ location or x, y, z, and θ location and using the defined and/or trained alignment features and parameters of step A1, all of which is shown as step C5, (6) focusing the camera 20 onto the wafer W if needed, all of which is shown as step C6 (7) collecting an image of the wafer W using the camera 20 by moving the plate 12 to align the camera with a first die or other portion thereof, viewing and recording that die or portion thereof by opening the shutter and allowing the camera to view and record the image, moving the plate 12 to align the camera with another die or portion thereof, viewing and recording this another die or portion thereof, and repeating these steps until all of the die or portions thereof on the wafer that are desired to be viewed have been viewed and recorded, all of which is shown as step C7, (8) simultaneously during step C7, determining where defects are located on the given die being viewed based upon the "good die" model of step A3 and the tolerances of step A4, all of which is step C8, and (9) creating a defect map of the wafer W which is a collection of all of the images of all of the die including all of the defects found thereon, all of which is step C9.

Alternatively, step C7 may be replaced by the step of collecting an image of the wafer W using the camera 20 by continuously moving the plate 12 so as to scan over all of the die on the wafer whereby the wafer is illuminated by a strobe light at a sequence correlating to the speed of the moving plate so that each die is strobed at the precise time it is under the camera 20. This allows for the continuous collecting of images without necessitating the stop and go procedure of aligning the camera with a first die, viewing and recording that die, moving the plate 12 to align the camera with another die, viewing and recording this another die, and repeating these steps until all of the die on the wafer have been viewed and recorded, etc.

Defect review D if and when it is desired (which is generally at the conclusion of defect inspection on a given wafer W since it is at this point that defect classification is often desired) involves (1) loading the defect map created in step C9, this reloading referred to as step D1, (2) selecting a defect to review (or alternatively reviewing all of the defects on the wafer in order) as step D2, (3) moving the plate 12 so as to position the wafer W such that the particular die with defect thereon is properly positioned under the camera 26, all of which is step D3, (4) user viewing and classifying of the defect such that user of the system 10 views and classifies the viewed defect, all of which is referred to as step D4, (5) repeating of steps D2–D4 until all of the defects that the user desires to review have been reviewed and classified as step D5, and (6) saving of classified defect map as step D6 as well as alternatively or additionally saving the defect information in any of a number of other formats for database or other management and review.

Defect reporting E if and when it is desired involves exporting or printing out the data stored in database format in step D6. This data may then be analyzed or otherwise used to perform statistical or other analysis on the types of defects, frequency of defects, location of defects, etc. which is useful to the wafer W manufacturers so as to allow them to focus on defect laden areas.

The above described steps and substeps are a basic explanation of the system and process of the present invention. The following description is a more detailed explanation of various parts and systems, and details of the steps these perform.

The wafer test plate 12 is a rotary stage that is equipped with a universal interface platform with vacuum, all of which provides a flexible interface for wafer and die package fixturing. It is defined such that it quickly mounts and inspects whole wafers, sawn wafers on film frame, die in gel pak, die in waffle-pak, MCM, JEDEC trays, Auer boats, and other wafer and die package arrangements and configurations.

The means for providing a wafer to the test plate referred to as 14 may be either manual in that the user moves the wafer from a cassette or magazine to the test plate 12, or automatic as is shown in the embodiment of the FIGS. In the automatic environment, the wafer providing means 14 includes a robotic arm that pivots from a first position where a wafer W is initially grasped from a magazine or cassette to a second position where the wafer W is positioned on the wafer test plate 12 for inspection. After inspection, the robotic arm pivots the wafer W from the second position at the test plate 12 back to the first position where the wafer W is placed back in or on the magazine or cassette.

The robotic arm in the embodiment shown is a two part arm which has two sections, the first of which pivots about a center support and the second of which pivots about the end of the first. Surrounding the robotic arm in one embodiment is at least one cassette receiver (two shown in FIG. 1) which receives standard wafer transportation cassettes in which multiple wafers are stacked, an optional wafer pre-aligner which would provide a pre-alignment or rough alignment of the wafer, and the inspection station which includes the wafer top plate 12, x-y-θ aligner 16, optics 18, cameras 20, etc.

The wafer alignment device 16 for aligning each and every wafer at the same x, y, z, and θ location is a precision system of rotary motors, ball screws, direct or belt driven motors, worm or other gears, actuators, hydraulics, push rods, vacuums, or other mechanical or electrical equipment for moving the rotary stage either linearly or angularly to a precise desired location.

The same alignment mechanism and process is used during training as is used during inspection. Specifically in the embodiment shown, the wafer alignment device is a 2-D x, y and θ alignment process that is optionally coupled to a z height control. Specifically, it is in one example a 2-D x and y course alignment followed by a fine theta (θ) alignment process, all of which is coupled with and followed by a focus map process (using a previously generated height or focus map) for determining height or z and thus assuring the wafer is in focus. Basically, the course alignment uses a pattern located at the approximate wafer center which it has been trained to know and expect x and y location on thereby allowing it to find this pattern and x and y (2-D linear) orient the wafer as such to at least course align it. This orientation is performed using the stage 12. Thereafter, fine alignment is performed by using a pattern near the perimeter of the wafer which it has been trained to know to get the θ (rotational) alignment correct. This is also performed using the stage 12. In both cases, the camera finds the pattern and the alignment mechanism moves the wafer until it is aligned.

The focus map or z orientation is performed by adjusting the camera and/or camera arm distance prior to focusing as is described below, and/or by changing objectives, and/or by focusing the camera. The adjustment that is performed is based upon a height map of the wafer from which focus is defined using pre-programmed points on the wafer.

The focusing mechanism 18 is an optical imaging mechanism with multiple optics therein for using different inspection resolutions. A motorized microscopic turret allows for selecting of the imaging optics from the multiple choices. For instance, a number of optics, such as three or five optics, may be supplied and typical choices include 1.25x, 2.5x, 5x, 10x, 20x, 50x and 100x objective The motorized microscopic turret and discrete objectives provide the means to select the optical magnification.

The camera system 20 or other visual inspection device is for visual inputting of good die during training and for visual inspection of other unknown quality die during inspection. The camera system may be any type of camera capable of high resolution inspection. An example of one part of such a camera system is a 3-CCD inspection camera used to capture die or other images during defect analysis.

One example of camera system 20 that is contemplated by the present invention is a two (2) camera system where one camera is an inspection camera and the other is a viewing camera. The inspection camera is a high resolution CCD camera that provides high resolution gray-scale images for inspection. The viewing camera is a high fidelity color image camera for visual review of found defects in, for example, 758×582 pixel resolution or alternatively 1008× 1018 pixel resolution or other known pixel sizes. In addition, the viewing camera provides high quality color images for operator defect review.

Computer controlled optics are provided that use long working distance microscopic objectives so as to provide for low distortion images that are required for accurate defect detection. Multiple magnifications may be automatically selected based on the user defined inspection recipes as described below.

Computer controlled illumination is integrated into and with the inspection camera and optics to complete the wafer imaging process. Alternatively, the illumination system may be coupled to the camera and optics so long as the illumination system works in conjunction with the camera. In a strobing environment as described herein, the illumination must occur simultaneously or substantially simultaneously with the camera shuttering which is in one example a high speed electronic shuttering mechanism; alternatively in a non-strobing environment, the illumination is typically continuous or as needed.

Illumination may be by any known illumination means such as high intensity lights, lasers, fluorescent lights, arc discharge lamps, incandescent lamps, etc. The angle of the illumination may be of a brightfield only, darkfield only, or both brightfield and darkfield variety.

Brightfield illumination involves illuminating the substrates from above where the illumination system is typically adjacent to or part of the camera which is mounted directly above the substrate, that is at approximately a 90° or so orientation to the substrate as shown in FIG. 1. In the embodiment shown, the brightfield illuminator is adjacent to the camera and functioning in unison therewith. This brightfield illumination is very effective in illuminating flat or relatively flat objects on a substrate as the light is reflected generally back to the camera. In contrast, 3-d objects on the substrate will angularly reflect the light causing the light to be angled away from the camera. As a result, flat objects appear bright to the camera while 3-d objects appear dark.

Darkfield illumination is often used in conjunction with the brightfield to "brighten" the 3-d objects, or in the alternative to only brightly see the 3-d objects. The darkfield light is provided at low angles to the wafer top plate 12. The darkfield illumination works inverse of the brightfield in that it reflects light up to the camera at an approximate 90° angle to the substrate when the darkfield light is introduced to 3-d object on the substrate at a low angle, while reflecting light at a low angle along the periphery opposite the light introduction where the object is flat. Darkfield light thus brightly illuminates 3-d objects while not illuminating flat objects very well.

Figure 20:
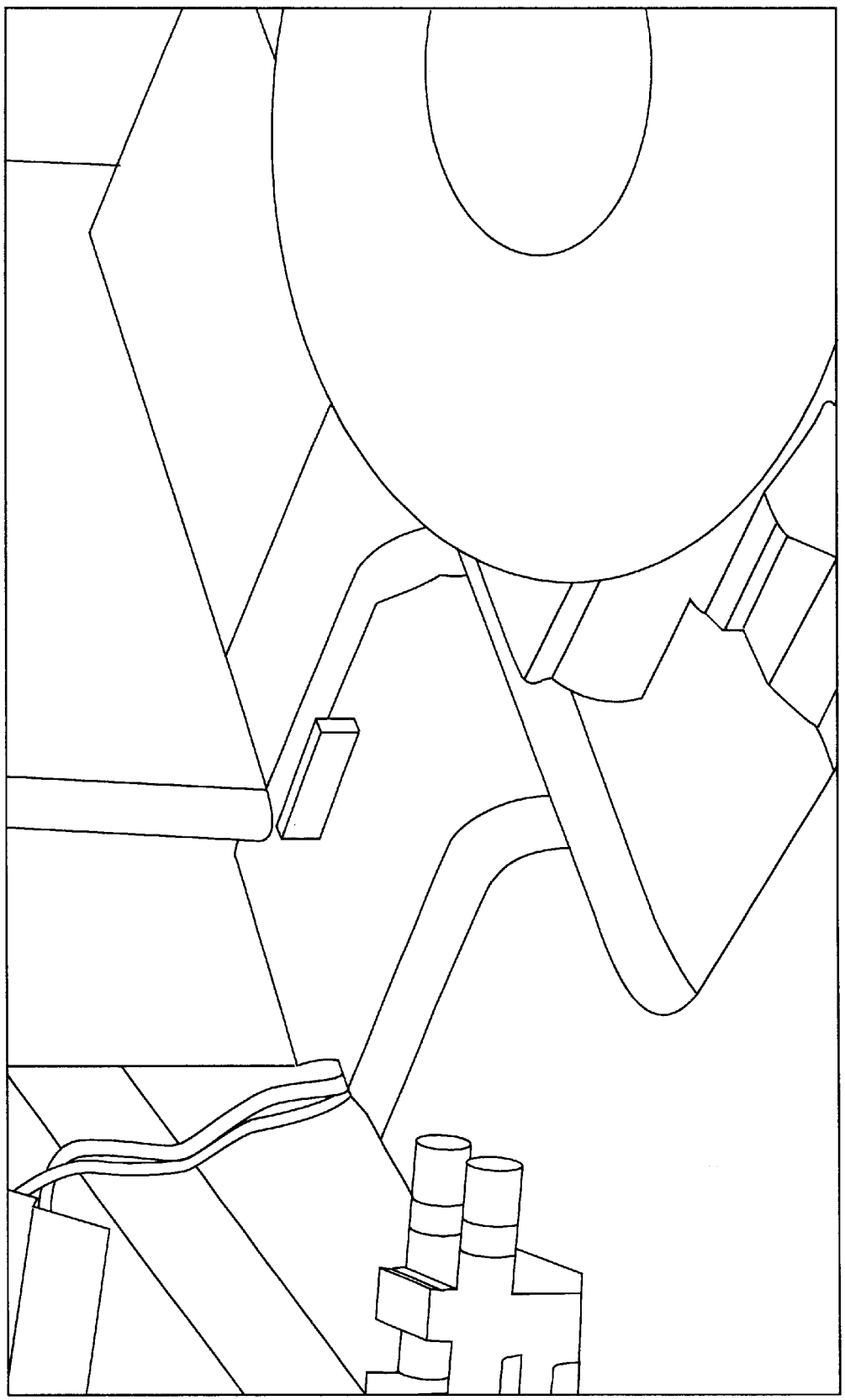
FIG. 20 is a partial view of the darkfield option of the present invention.
Figure 21:
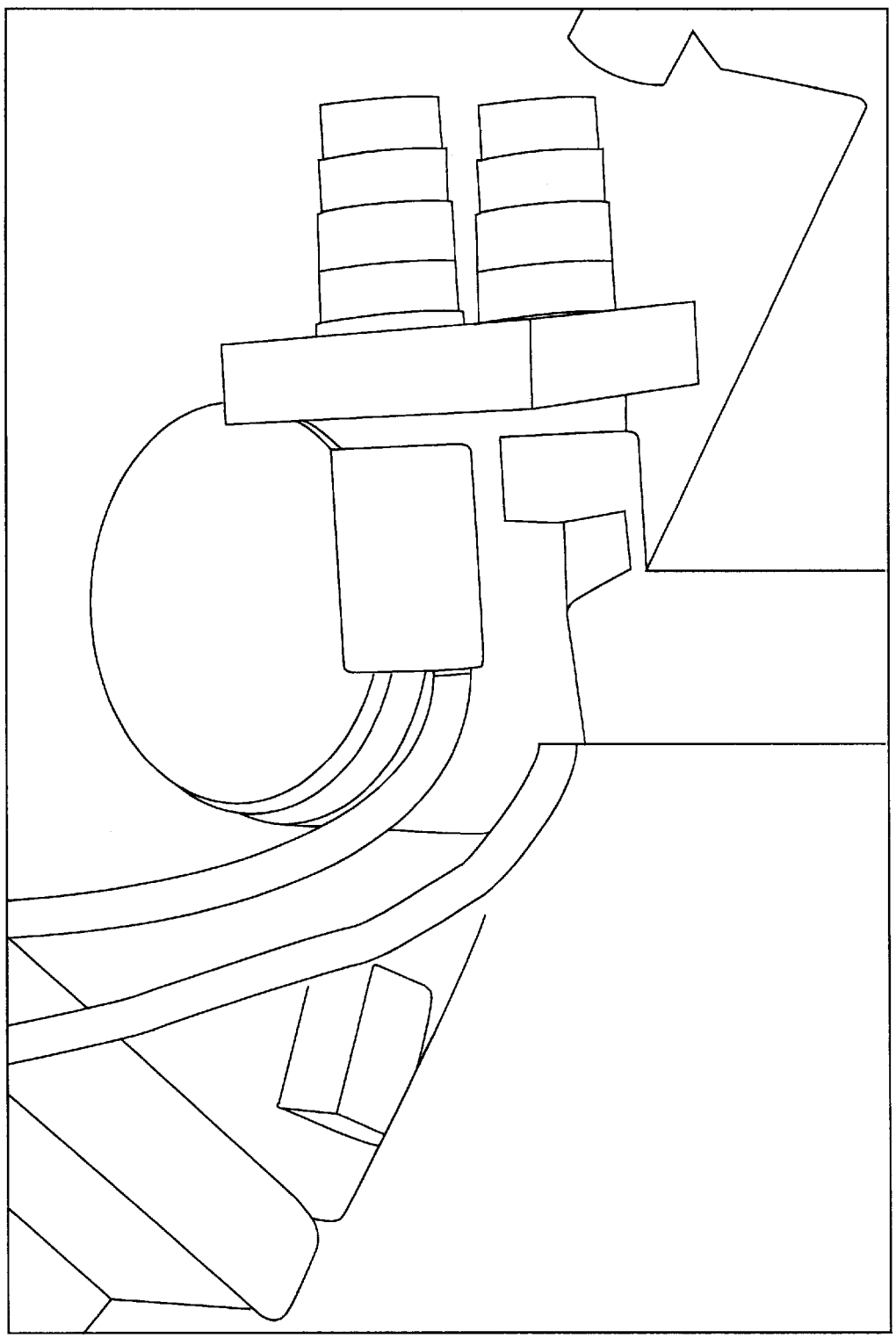
FIG. 21 is an enlarged view of the darkfield lasers of the darkfield option.

The system 10 with a darkfield option as shown best in FIGS. 20–21 to include a plurality of illuminators spaced about the periphery. In one example four illuminators are used and each is equally spaced from the other at a 90° separation. In another example (FIGS. 20–21 where one pair are shown), eight illuminators are used at a 45° separation, and in an alternative associated therewith and shown in the drawings, the illuminators are teamed up in pairs at 90° separation to double the capacity of the illuminators at a given angle.

The user, where the system is equipped with both brightfield and darkfield illumination, has the option of using one or the other or both. This provides significant options. For instance, if the inspection is being performed on die that tend to only have flat objects thereon, brightfield illuminates these objects well and is more than sufficient for this type of inspection. Alternatively, if the inspection is being performed on die that tend to have 3-d objects, then darkfield may be sufficient. However, as in many cases, such as with gold bumps which are generally very flat but very rough and tend to include 3-d nodules protruding therefrom, a combination of the two is often beneficial. In this example, the brightfield illumination indicates the presence of any defects such as scratches, etc. and the presence of the bump while the darkfield illumination shows the nodules and rough surface on the bump. Without the darkfield, the bump shows up as a dark image. Once darkfield is introduced, the nodules are located as white spots on the bump.

Darkfield also assists in defect classification because brightfield light does not differentiate between a particle or defect that extends from the surface versus one that is embedded or scratched into the surface. Darkfield illumination does differentiate these extending versus embedded defects.

In one embodiment, the system 10 includes a brightfield illumination system that is physically located adjacent to or incorporated physically into the camera so as to provide brightfield illumination from above the objects illuminated. In another embodiment, the system 10 includes a darkfield illumination system that is located peripherally around the wafer top plate 12 at low angles of difference from the top plate, angles such as 1° to 10°. In an even further embodiment, both brightfield illumination from above the object and darkfield illumination from around the periphery of the object are provided. As indicated above, the illumination as provided by the brightfield and darkfield illumination systems may be provided by any known illumination source such as a white light source such as incandescent, fluorescent, or other similar gas envelope or similar electrical lights, or by lasers or similar devices.

The parameter input device 22 is for inputting parameters and other constraints or information. These parameters, constraints and information include sensitivity parameters, geometry, die size, die shape, die pitch, number of rows, number of columns, etc. It is contemplated that any form of input device will suffice including a keyboard, mouse, scanner, infared or radio frequency transmitter and receiver, etc.

The display 24 is for displaying the view being seen by the camera presently or at any previous saved period. The display is preferably a color monitor or other device for displaying a color display format of the image being viewed by the camera 20 for the user's viewing, or alternatively viewing an image saved in memory. This monitor, or another adjacent or other monitor may be used to view the gray-scale inspection image of the camera 20 that iis being used by the system 10. This display 24 is used during inspection to show the image being viewed by the camera 20. In addition, the system parameters display 36 is also available for displaying other information as desired by the user such as system parameters.

The computer system 26 or other computer having processing and memory capabilities is for saving the inputted good die, developing a model therefrom, and comparing or analyzing other die in comparison to the model based upon defect filtering and sensitivity parameters to determine if defects exist. The computer system 26 is also used to perform all other mathematical and statistical functions as well as all operations. In one embodiment, the computer system 26 is of a parallel processing DSP environment.

The marking head 28 is provided for marking a particular die such as a defective one. In one embodiment, the marking head is a die inking mechanism. It is used whereby each die may be inked after inspection, or all defective die may be inked, or all defective die may be inked after review and/or classification, etc. Inking may also be used in a "forced inking" manner whereby pre-specified die are inked regardless of electrical or visual inspection such as all die at the edge of the wafer.

An air knife is optionally provided for cleaning the wafers prior to inspection. The air knife is basically a conduit of some design through which air may be injected where the conduit includes one or more orifices or outlets. The air is projected out of the orifices which are selectively positioned on the conduit and in relation to the wafer so as to blow dust and other particles off of the wafer prior to review. This eliminates false defect determinations.

These systems and parts are part of system 10 and are used to perform the defect inspection. This defect inspection is briefly described above, and is now described below in detail.

The overall training step A is described below in more detail.

The step A1 is defining and/or training alignment features and parameters (and storing) in the computer system 26 for use during training. This alignment technique, when performed in step A3 and C5 as described below to define a good die and to inspect, is a two function process, namely a physical alignment and an image alignment. At this point we define what parameters are to be used during the physical and image alignment. These parameters include defining markers as are needed during physical alignment, and distinct elements and buffers as are needed during image alignment. The actual physical and image alignment steps occur during step A3 and C5 as described below.

The step A2 is defining (and inputting into the computer system) the wafer and/or die geometry, the wafer and/or die sizes, the die pitch, the number of rows, the number of columns, etc. and storing all such information in the computer system 26 for use during training and/or inspecting.

The step A3 is training the system as to what a "good die" comprises by aligning via device 16 and viewing via camera 20 a plurality of known good die and forming a model within computer system 26 to define what an ideal die should look like based upon the common characteristics, elements, ranges, etc. viewed. A good die is defined as a die that does not have defects but may very well and is actually likely to have process variations in it; however all of these process variations have been deemed not to be defects and rather to be acceptable variations. Preferably, the entire or full spectrum of acceptable random deviations is supplied by this training set of typically twenty, thirty or up to one hundred good die that are shown to the system during training, although no minimum or maximum is required. However, the larger the pool the more accurate the results because a better, more diverse model is created. Thus color drifts and contrast shifts as well as many other deviations would be part of the training set. Basically, the system 10 performs die inspection by studying a user provided set of known good die.

The alignment may involve either physical alignment or image alignment, or both. Physical alignment basically involves inputting specific location markers on or around each wafer, die or sub-section of die which are used as location points from which the wafer and die are located and aligned. At step A1, these markers were defined.

Physical alignment involves the wafer test plate 12 via the wafer alignment device 16 aligning each and every wafer, die, etc. in the same x, y, and θ location by looking for and aligning with these location markers. In use, the system takes an overall picture or image of the wafer, die or sub-section thereof and looks for the specific location markers. The system uses a hunting method to find the markers. Once one or more specific location markers are identified, and it is found that the markers are in some other location or orientation than expected, then the wafer test plate 12 spins, turns, adjusts or otherwise moves in a translational or rotational manner in the x, y, and θ directions the wafer, die or sub-section.

The system also may perform image alignment. During step A1, distinct elements and buffers, as are needed in image alignment, were defined.

This image alignment may also be referred to as software alignment as the software actually performs the alignment by aligning the image that is taken rather than physically moving the wafer or die. This image alignment is performed on each section of the wafer, such as each die, during one or both the good die modeling and the unknown quality die inspecting. It is often necessary because each image taken may be off slightly in comparison to adjacent images or to a common location on another wafer. The actual process of image alignment basically assures that all images taken of a particular location will align, that is when overlapped the features of the images will align, rather than have an offset or twist, so that only defects stick out.

Image alignment, when performed as needed in steps A3 and/or C5, involves the camera looking for a distinct element on the die from which to turn or move the image to "square" it up. The distinct element is generally an element large enough that defects therein will not be an issue. The element also must be of a distinct shape. If the distinct element is where we expect it to be then the image lines up and no image alignment is necessary; however, it is not, then the distinct element must be found and the image adjusted.

The hunting for the distinct element in image alignment may be performed on the entire die. However, this is expensive and time consuming. As a result, smart alignment may alternatively be performed.

With smart alignment, a buffer is defined into the image. This buffer allows for "wiggle", that is movement or twisting in the image. This buffer is typically an x amount and a y amount of movement that is expected. This buffer is then used to define the area around the expected location of the distinct element to be searched for the distinct element. Once the distinct element is found, then the x and y distance that the distinct element is off from the expected distinct element location is the distance the entire image is moved in the x and y direction to align the image.

The viewing encompasses collecting an image of the wafer W, a known good wafer, using the camera 20 by moving the plate 12 to align the camera with a first image which may be the whole wafer, a part of the wafer, a die, or a part of a die and then viewing and recording that image. Thereafter moving the plate 12 to align the camera with another image, viewing and recording this another image, and repeating these steps until all of the images on the wafer have been viewed and recorded. An alternative step C8 involves continuous motion and strobe illumination as is described below. In either case, this is then repeated for a plurality of known good die or wafers as viewing of a pool of wafers is necessary to form a model of a good die.

The actual defect inspection algorithm is calculated from the collection of images of the set of "good die". An image or images are taken of each good die in a set of good die. Each image is composed of pixels such as for example an approximately one thousand by one thousand (1000×1000) array or grid of pixels, although any number may be used. For each same pixel on all of the good die images, that is for each common x,y coordinate, which is a pixel, a mean and standard deviation is calculated of the pixel value, that is the gray-scale value of that given pixel. So in a grouping of 30 good die, as used as an example above, where each die is an array of 1000×1000 spots (1 million total spots) each referred to as a pixel, a mean and a standard deviation of the gray-scale number for each pixel at x,y coordinate 1×1, 1×2, 1×3 and so on all the way to 1000×1000 is calculated; that is a mean and standard deviation is calculated for pixel 1×1 using the gray scale measurement for pixel 1×1 on all 30 die, and so on for each of the 1 million die.

In one embodiment, the gray scale numbers for each pixel, are used to calculate the mean and standard deviation, and these are in a range. One example is a 256 scale scheme, where one end, such as 0 in the 256 scale scheme, represents a dark or black colored or shaded image and the other end, such as 255 in the same 256 scale scheme, represents a white colored or shaded image.

The collection of all of the means, that is for all of the pixels, for a type of die is in effect the perfect die of that type and in essence defines the good die model. The collection of all of the standard deviations, as adjusted as described below for sensitivity and filtering, for a type of die is in effect the allowable range inside of which the die is deemed good, and outside of which the die is questioned as to defects.

The step A4 is setting inspection parameters which are values that indicate to the computer system 26 how close an unknown quality die must match the good die model to be considered a good die (that is, what differences from the exact model are tolerable to still be considered a good die). Several such inspection parameters are defect sensitivity, minimum defect contrast and defect filtering.

In the embodiment shown defect resolution is dependent upon the optical magnification. Selecting a higher magnification results in a smaller field of view of the image. The magnification selected may result that multiple images are required to inspect a single die or that many can fit in a single image. The die size and optical magnification are inputted in step A2. It is however noted that smaller defect resolution results in more imaging per die and thus additional time to defect inspect the same quantity of die. Alternatively, a camera with adjustable resolution may be implemented whereby this adjustment feature would control sensitivity rather than image size.

Defect sensitivity involves user defined multiplication factors of the mean and standard deviations calculated to define the known good die model as described above. Defect sensitivity is described below in more detail in step C7.

Minimum defect contrasting involves user defined absolute limits on the upper and lower limits defined from the mean and standard deviation. Minimum defect sensitivity is also described below in more detail in step C7.

Defect filtering involves statistical or data filtering including area, size, region of interest and/or clustering filtering, as well as connection and/or reduction factor filtering. This filtering allows the user to filter out items that appear as defects but are not in critical areas, of sufficient size or shape or are otherwise acceptable and thus desirable to not be labeled as defects. In the embodiment shown, defect filtering is provided for each inspection recipe or round. This allows the system performance to be optimized for the user's application. The defect filtering feature uses defect position and geometry information such as shape, size, x-y coordinates, etc. to automatically determine if the defect requires further review and classification by the operator. An example is as follows, any defects above a certain size may be determined to be positively defects not subject to further review. In addition or as an alternative, any defects below a certain size are filtered out as not being a defect although being outside of the "good die" model. There may also be an area in between that requires operator review at the review steps of step D4. Similarly, shapes, positions, configurations, arrangements, etc. of anomalies from the "good die" model may be filtered. Defect filtering is further defined below.

The step A5 is saving this training model and its features, parameters, etc. to the computer system 26.

The overall inspection recipe creating step B involves creating and storing an inspection recipe for each type of item, that is wafer, die, etc. to be inspected. An unlimited number of inspection recipes can be created, copied and edited so as to allow the user to customize the inspection process.

The step B1 is defining how wafers W are selected from cassettes or other storage receptacles. The step B2 is defining how the dies on each wafer W are to be selected for defect inspection. The step B3 is defining how defect inspection map files are imported and exported. The step B4 is saving this recipe.

The overall inspecting step C, referred to as defect inspection, is an advanced proprietary digital image analysis technique for semiconductor wafer inspection. The system performs wafer inspection after first studying a user provided set of known good die as described above in step A3. This method of learning and inspecting is more powerful than traditional template or model matching inspection. It is noteworthy that even random variations in a known good die may be determined to be acceptable which is not the case with traditional template or model matching. In effect, this robust approach to wafer inspection functions similar to a human operator without the fatigue and other problems.

The step C1 is inputting a wafer identification code if desired. This is required where wafer mapping is to occur because this provides a way to identify each wafer for later review of defects, etc. The wafer identification code may be of any known identification system such as alphanumeric characters, bar codes, 2-D matrix codes, etc.

The step C2 is selecting a recipe that was defined in step B. The step C3 is selecting a product setup if one is desired.

The step C4 is loading a wafer onto the wafer test plate 12 using the wafer providing means 14. Loading onto the wafer test plate may be either by manual loading or using an automatic system where wafer with die thereon are automatically transferred from a cassette or magazine into the inspection area. The automatic system allows for elimination of all manual handling.

The step C5 is aligning the wafer on the wafer test plate 12 using the wafer alignment device 16 for aligning each and every wafer at the same x, y, z, and θ location and using the defined and/or trained alignment features and parameters of step A1. This has been described above in detail as the same process of physical alignment and image alignment is used here as was used to align the known good wafers to form the good die model.

It is often also necessary to focus the camera 20 onto the wafer W if it is not already focused. This occurs, if needed, during or after step C5 and is the z orienting of the wafer which is defined by a height map.

The step C6 is collecting an image of the wafer W using the camera 20 by moving the plate 12 to align the camera with a first image which may be the whole wafer, a part of the wafer, a die, or a part of a die and then viewing and recording that image, and thereafter moving the plate 12 to align the camera with another image, viewing and recording this another image, and repeating these steps until all of the images on the wafer have been viewed and recorded. An alternative step C6 involves continuous motion and strobe illumination as is described below.

The step C7 is simultaneous with step C6 and involves determining where defects are located on the given die being viewed based upon the "good die" model of step A3 and the tolerances or parameters of step, A4. Basically, each pixel on the unknown quality wafer is viewed whereby defect sensitivity and filtering are used in conjunction with the "good die" model to determine if the pixel and/or any group of pixels are deemed "good" or questionable.

Initially anomalies or differences between the "good die" model and the image are spotted and then sensitized and filtered. To simplify the determination, an upper level and lower level value is determined for each pixel on each die, based upon the mean and standard deviation calculations as well as the user defined sensitivity and absolute limits. The viewed image is then filtered using one or more of a variety of filter techniques including connection factoring, reduction or noise reducing factoring, and statistical or data filtering on blob identification such as area, size, region of interest, and/or interactive filtering. After filtering, the questionable defect areas are identified. Basically, defect sensitivity and minimum defect contrast are used to define the upper and lower level values which are in effect the adjusted standard deviations on either side of the mean once the sensitivity is factored in. Thereafter, filtering is often used to better identify true defects.

In one embodiment, defect sensitivity is basically a user defined multiple of the standard deviation. Through actual analysis of good and bad die, the user defines a multiple of the standard deviation that most accurately defines all of the defects yet does not wrongly define good die as defects. An example is as follows. Assume three known good die with gray scale values of 98, 100 and 102. The mean is 100 and the standard deviation is ±2. The user through inspection knowledge defines the defect sensitivity at 5. The upper and lower limits are then 110 and 90 respectively.

In one embodiment, the minimum defect contrast is similarly a user defined absolute limit. In the above example, the user through knowledge is aware that gray scale measurements with a minimum contrast of 15 are not defective. The minimum defect contrast is thus set at 15 and as a result the upper and lower limit must be 115 and 85 instead.

In the preferred embodiment, a test image is created using simple image subtraction after each pixel of an unknown quality wafer or die is viewed. A test image is created by basically subtracting the gray scale measurement of the test pixel, for example 98, from the good die upper limit, for example 110, for that pixel, or subtracting the good die lower limit, for example 90, from the gray scale measurement of the test pixel, again 98, to get a binary good or bad indication. The upper and lower limits have preferably been sensitized. If the number is positive then it is colored black as being inside the range (or alternatively white), and if the number is negative then it is colored white as being outside of the range (or alternatively black). A binary black and white image results. This image allows for filtering at a much more rapid speed due to its simplicity in comparison to saving an actual 256 color image. Alternatively, a full color, such as 256 color, image may be used if sufficient memory is available and optimal speed is not vital.

In one embodiment, one or more of the following filters are used on the binary black and white image. Image processing functions such as connection factoring and reduction factoring may then individually or all together be used. Statistical or data filtering on blob identification may also be performed individually or all together.

Connection factoring involves a "close" operation. The identified pixels, in the above example the white one, are dilated and then eroded, or double dilated and then eroded, or any other known combination. This connects or fills in the defects so as to filter out small defects or acceptable irregularities.

Reduction factoring involves an "open" operation. The identified pixels are eroded and then dilated, or double eroded and then double dilated, or any other known combination. This reduces noise.

Blob analysis involves identifying blobs on the binary black and white image. Once identified, various parameters of each are identified including, for example, size such as x size and y size, location, area, etc. Statistical or data filtering is then performed on the parameters of the blobs.

Such statistical or data filtering includes area filtering, size filtering, region of interest filtering, and interactive defect classification filtering. Area filtering discards blobs of a pre-set area or smaller. Size filtering discards blobs of a pre-set x or y size or smaller. Region of interest filtering allows the user to define locations on the die that are not of as much or any importance and as such any defects thereon would be irrelevant. Finally, interactive defect classification involves clustering of close but not touching identified pixels where the distance defining close is user defined.

Basically, the unknown quality die are inspected by viewing the image and comparing each pixel with its mean and standard deviation via the upper and lower limit values. Sensitivity and filtering also allows for compensation for factors that are deemed by the user to be more or less critical. In sum, if any one of the given viewed pixels in the unknown quality die is outside of the upper and lower limit values as sensitized and filtered, then the die is defective and as described below, that defective spot is inked or otherwise noted.

The step C8 is creating a defect map of the wafer W which is a collection of all of the defect data of all of the die and is stored in a data file. In the preferred embodiment, it is a binary black and white image.

As an alternative to the above described inspection steps, the alternative step C6 which is the step of collecting an image of the wafer W using the camera 20 by continuously moving the plate 12 so as to scan over all of the die on the wafer whereby the wafer is illuminated by a strobe light at a sequence correlating to the speed of the moving plate so that each die is strobed at the precise time it is under the camera 20. Basically a short illumination pulse of light on the moving plate effectively "freezes" the image. This allows for the continuous collecting of images without necessitating the stop and go procedure of aligning the camera with a first die, viewing and recording that die, moving the plate 12 to align the camera with another die, viewing and recording this another die, and repeating these steps until all of the die on the wafer have been viewed and recorded, etc.

The overall defect review step D is generally at the conclusion of defect inspection on a given wafer W since it is at this point that defect classification is often desired. The defect inspection or detection process of steps C is all automatic and rapid whereby once complete the user may manually inspect only the defects found based upon the parameters, filters, sensitivities, etc. rather than all of the die or wafer for defects. Significant time is saved.

The step D1 is loading the defect map created in step C9. The step D2 is selecting a defect to review (or alternatively reviewing all of the defects on the wafer in order). The step D3 is moving the plate 12 so as to position the wafer W such that the particular defect is properly positioned under the camera 26. The step D4 is user viewing and classifying of the defect such that user of the system 10 views and classifies the viewed defect. Any number of classifications are available and the classifications are user defined. The step D5 is repeating of steps D2–D4 until all of the defects have been reviewed and classified. The step D6 is saving of classified defect map as well as alternatively or additionally saving the defect information in any of a number of other formats for database or other management and review.

The overall defect reporting step E is exporting or printing out the data stored in database format. This data may then be analyzed or otherwise used to perform statistical or other analysis on the types of defects, frequency of defects, location of defects, etc. which is useful to the wafer W manufacturers so as to allow them to focus on defect laden areas. This step E provides for complete and effective data analysis as it reports data in multiple formats including graphical, tabular, and actual image displays. The data that is placed in tabular format allows numerical values to be readily correlated with other values such as electrical formats. The graphical data representation quickly shows trends that would otherwise be difficult to see.

The system 10 is based upon standard computer technology such as Pentium® Pro or similar computer platforms which allow for many different communication options of for example both a serial and network format. For instance, the system includes TCP/IP configuration and may alternatively include SEC-II/GEM or other computer industry standard protocols.

The system 10 may also be used to perform an inspection using a drift map. This is useful where the individual die of the wafer W are cut up on a film and stretched as needed for picking up and removal therefrom as is well known in the art. The problem here is that during stretching, the orthogonality may be lost and the die move in different directions and ways as the film material unevenly stretches. The approximately square or rectangular cut dies are now oriented in all different directions and as such a row of die is no longer straight but rather wavy or otherwise disoriented. When this drastic stretching and loss of orthogonality occurs, a drift map and drift step is added to account for this. This step is typically inserted prior to scanning.

In one embodiment, a frame grid is created for the purpose of defining the expected location of each die. It is known to stretch the film sawn wafers are transported on so as to allow easier picking up of each die without damaging neighbor die. This stretching however is typically not uniform resulting in disoriented die. The drift map predicts the stretched location of each die using the starting point of the die which was known due to the rigidity before sawing, and the pitch.

To create a drift map, a mark or dummy die is placed on the wafer at every nth location, such as every $10^{th}$. Using machine vision, the system 10 looks for the mark at its expected location and then looks therearound if not found. Once the actual location is found, the machine vision proceeds to the expected location of the next mark and reiterates through the process. Once all of the marks have been found, a pitch is calculated assuming consistent behavior in between marks. Using this pitch and knowing the original location of each die prior to sawing, a drift map is created which accurately predicts the location of the die.

The system 10 may also incorporate use of an autofocus feature. Such a feature is based upon a sharpness calculation where a sweep of the image is taken at each of a predefined picture point. Thereafter, a sharpness calculation is used to find the correct focus point. To save time, this may be performed on only every nth image.

In sum, the basic sequence of operation is as follows, with the automated wafer transfer and wafer mapping options removed. The operator or user must first train the system as to what a "good die" is, that is create a good die model, or choose an existing good die model. As indicated above, this involves inputting and using location markers to properly align a plurality of known good die such that each die is imaged from the exact same x, y, z and θ location. In addition, wafer and/or die geometry, sizes, pitch, number of rows, number of columns, etc. must be inputted prior to imaging of good die. The plurality of good die are then each aligned and viewed by the CCD camera such that the computer system then forms a "good die" model by grouping all of the common characteristics, noting the ranges of pitches, colors, angles, locations, etc. Basically, the system 10 performs wafer inspection by studying a user provided set of known good die. It is generally preferred that at least twenty or thirty die are provided, although no minimum or maximum is required. Inspection parameters are also set to indicate how close an unknown quality die must match specific characteristics of the "good die" model to be considered a good die. These include sensitivity parameters and defect filters.

The user must also create or select a previously stored inspection recipe. This includes information as to how wafers W are selected from cassettes or other storage receptacles, how the dies on each wafer W are to be selected for defect inspection, how defect inspection map files are imported and exported, etc.

The system 10 is now ready to inspect unknown quality die. If identification codes are being used as are necessary where wafer mapping is active, one must be inputted at this point. Thereafter, a wafer W (or sawn wafer, or die in gel-pak, or die in waffle pak, etc.) is loaded onto the inspection area and specifically the wafer test plate 12 (which is under the inspection camera). This is accomplished using the wafer providing means 14. Thereafter, the wafer alignment device 16 aligns the wafer at the same x, y, z, and θ location as the "good die" were loaded by using the defined and/or trained alignment features and parameters of step A1. The magnification desired is then selected and thereafter the camera 20 is focused.

The system is now ready to collect an image of the selected area (the first die position) of the wafer W using the camera 20 by moving the plate 12 to align the camera with the selected area, such as a first die position, so as to take a first image thereof which may be the whole wafer, a part of the wafer, a die, or a part of a die and then viewing and recording that image. Automatic defect inspection and bond pad analysis are performed on the die's digital image. If the die is inked, it is automatically identified (mapped) as an "inked die". If the die is not inked, and a defect was found, then the system will collect and store detailed information about each defect such as defect location on the die, size, shape, etc.

The plate 12 is then moved to align the camera with another selected area, which may be the next adjacent area or not, to take an image thereof (the second die position) on the wafer adjacent to the first image. Basically, the plate is indexed under the inspection camera to the next die position. This second die position is then viewed and recorded. These steps are repeated until all of the images on the wafer have been viewed and recorded. Simultaneous with these image viewing steps, defect sensitivity and filtering are used in conjunction with the "good die" model viewing to determine if initial anomalies or differences between the "good die" model and the image are actual defects or if they should be filtered out. A defect map of the wafer W is then created in the computer system from the collection of all of the defect of all of the die including all of the defects found thereon.

In another embodiment, rather than move the plate in incremental steps, the plate is continuously moved during strobe illumination thereof. The sections of the wafer are then scanned by synchronizing the camera with a strobe illumination so that when the camera is properly positioned over each section of the moving substrate, the strobe illumination occurs simultaneous with the image collection via the camera.

At the conclusion of defect inspection on a given wafer W, defect classification is often desired. Each archived defect is manually reviewed by the user where the plate 12 is moved to the position on the wafer W that the particular defect is positioned at so that the user may view and classify the defect. This is then repeated for all defects. The classified defects are then saved as a classified defect map.

That wafer is then removed and another wafer is loaded for inspection. This removal and loading of a new is either manually performed or may be automatically performed.

Accordingly, the invention as described above and understood by one of skill in the art is simplified, provides an effective, safe, inexpensive, and efficient device, system and process which achieves all the enumerated objectives, provides for eliminating difficulties encountered with prior devices, systems and processes, and solves problems and obtains new results in the art.

In the foregoing description, certain terms have been used for brevity, clearness and understanding; but no unnecessary limitations are to be implied therefrom beyond the requirement of the prior art, because such terms are used for descriptive purposes and are intended to be broadly construed.

Moreover, the invention's description and illustration is by way of example, and the invention's scope is not limited to the exact details shown or described.

Having now described the features, discoveries and principles of the invention, the manner in which it is constructed and used, the characteristics of the construction, and the advantageous, new and useful results obtained; the new and useful structures, devices, elements, arrangements, parts and combinations, are set forth in the appended claims.

We claim:

1. An automated method of inspecting a semiconductor wafer in any form including whole patterned wafers, sawn wafers, broken wafers, and wafers of any kind on film frames, dies, die in gel paks, die in waffle paks, multi-chip modules often called MCMs, JEDEC trays, Auer boats, and other wafer and die package configurations for defects, the method comprising:

training a model as to parameters of a good wafer via optical viewing of multiple known good wafers, the training including aligning and viewing the multiple known good wafers, taking a gray scale measurement of each pixel in a grid of pixels on each of the multiple known good wafers, calculating the mean and standard deviation of all of the gray scale measurements for each pixel location on the multiple known good wafers, and then determining an upper and lower limit for each pixel location in between which a gray scale measurement on an equivalent pixel on an unknown quality wafer is deemed good while a gray scale measurement on an equivalent pixel on an unknown quality wafer outside of the upper and lower limits is deemed of at least questionable integrity and so noted, the upper limit being calculated as the maximum of one of the mean plus the product of the standard deviation multiplied by a first sensitivity, or the mean plus a first minimum contrast, and the lower limit being calculated as the minimum of one of the mean minus the product of the standard deviation multiplied by a second sensitivity, or the mean plus a second minimum contrast; and inspecting unknown quality wafers using the model, where such inspecting involves calculating the gray scale measurement for each pixel on the unknown quality wafer and comparing the gray scale measurement of each pixel with the upper and lower limit for that given pixel location to determine if the gray scale measurement for that pixel is between the upper and lower limits and thus deemed good or is outside of a range between the upper and lower limits and thus deemed of at least questionable integrity.

2. The automated inspection method of claim 1 wherein the training a model step includes aligning and viewing via a camera the multiple known good wafers.

3. The automated inspection method of claim 1 wherein the training model step further includes taking the gray scale measurement of each pixel on a 0 to 255 gray scale.

4. The automated inspection method of claim 1 further comprising training a system as to inspection parameters which are values that indicate how many standard deviations away from the mean are acceptable in defining the upper and lower limits.

5. The automated inspection method of claim 1 further comprising training a system as to alignment features and parameters of wafers.

6. The automated inspection method of claim 1 further comprising training a system as to at least one of the following: wafer geometry, wafer size, die geometry on a wafer, die size on a wafer, number of rows of die on a wafer, and number of columns of die on a wafer.

7. The automated inspection method of claim 1 further comprising training a system as to inspection parameters.

8. The automated inspection method of claim 1 further comprising creating an inspection recipe that is used during inspecting to perform at least one of the following: defining how substrates are selected from storage receptacles, defining how dies on a wafer are selected for defect inspection, and defining how an inspection map is imported or exported, if needed.

9. The method of claim 1 further comprising defect reviewing following the completion of inspecting whereby only die failing to meet the good wafer model are reviewed.

10. An automated method of inspecting a die on a substrate such as a wafer in any form including whole patterned wafers, sawn wafers, broken wafers, and wafers of any kind on film frames, dies, die in gel paks, die in waffle paks, multi-chip modules often called MCMs, JEDEC trays, Auer boats, and other wafer and die package configurations for defects, the method comprising:

training a model as to parameters of a good die via optical viewing of multiple known good die, the training including aligning and viewing the multiple known good die, taking a gray scale measurement of each pixel in a grid of pixels on each of the multiple known good die, calculating the mean and standard deviation of all of the gray scale measurements for each pixel location on the multiple known good die, and then determining an upper and lower limit for each pixel location in between which a gray scale measurement on an equivalent pixel on an unknown quality die is deemed good while a gray scale measurement on an equivalent pixel on an unknown quality die outside of the upper and lower limits is deemed of at least questionable integrity and so noted, the upper limit being calculated as the maximum of one of the mean plus the product of the standard deviation multiplied by a first sensitivity, or the mean plus a first minimum contrast, and the lower limit being calculated as the minimum of one of the mean minus the product of the standard deviation multiplied by a second sensitivity, or the mean plus a second minimum contrast; and inspecting unknown quality die using the model, where such inspecting involves calculating the gray scale measurement for each pixel on the unknown quality die and comparing the gray scale measurement of each pixel with the upper and lower limit for that given pixel location to determine if the gray scale measurement for that pixel is between the upper and lower limits and thus deemed good or is outside of a range between the upper and lower limits and thus deemed of at least questionable integrity.

11. The automated inspection method of claim 10 wherein the aligning and viewing is performed via a camera.

12. The automated inspection method of claim 10 wherein the training model step further includes taking the gray scale measurement of each pixel on a 0 to 255 gray scale.

13. The automated inspection method of claim 10 further comprising training a system as to inspection parameters which are values that indicate how many standard deviations away from the mean are acceptable in defining the upper and lower limits.

14. An automated method of inspecting a substrate such as a wafer in any form including bare wafers, whole wafers, patterned wafers, sawn wafers, and wafers of any kind on film frames, dies, die in gel paks, die in waffle paks, multi-chip modules often called MCMs, JEDEC trays, Auer boats, and other water and die package configurations for defects, the method comprising:

determining an upper and a lower limit for each pixel on a substrate divided into a grid of pixels, the upper and lower limits for each pixel being calculated as a relationship of a plurality of visually perceived contrasts for that pixel on a plurality of substrates known as good quality substrates and specifically as the upper limit is a maximum of one of a mean of the visually perceived contrast for a given pixel plus a product of a standard deviation of the visually perceived contrast for the given pixel multiplied by a first sensitivity, or the mean for the given pixel plus a first minimum contrast for the given pixel, and the lower limit is a minimum of one of the mean of the visually perceived contrast for a given pixel plus a product of the standard deviation of the visually perceived contrast for the given pixel multiplied by a second sensitivity, or the mean for the given pixel plus a second minimum contrast for the given pixel:

comparing a visually perceived contrast, for each pixel from an unknown quality substrate with the upper and lower limit for that pixel; and categorizing each compared pixel as either good if Its visually perceived contrast is between the upper and lower limit, or bad if its visually perceived contrast is outside of the upper and lower limit.

15. An automated method of inspecting a substrate such as a wafer in any form including bare wafers, whole wafers, patterned wafers, sawn wafers, and wafers of any kind on film frames, dies, die in gel paks, die in waffle paks, multi-chip modules often called MCMs, JEDEC trays, Auer boats, and other wafer and die package configurations for defects, the method comprising:

determining an upper and a lower limit for each pixel on a substrate divided into a grid of pixels, the upper and lower limits for each pixel being calculated as a relationship of a gray scale measurement for that pixel on a plurality of substrates known as good quality substrates, and specifically as the upper limit is a maximum of one of a mean of the gray scale measurement for a given pixel plus a product of a standard deviation of the gray scale measurement for the given pixel multiplied by a first sensitivity, or the mean for the given pixel plus a first minimum contrast for the given pixel, and the lower limit is a minimum of one of the mean of the gray scale measurement for a given pixel plus a product of the standard deviation of the gray. scale measurement for the given pixel multiplied by a second sensitivity, or the mean for the given pixel plus a second minimum contrast for the given pixel;

comparing a gray scale measurement for each pixel from an unknown quality substrate with the upper and lower limit for that pixel; and categorizing each compared pixel as either good if its gray scale measurement is between the upper and lower limit, or bad if its gray scale measurement is outside of the upper and lower limit.

16. An automated method of inspecting a substrate such as a wafer in any form including bare wafers, whole wafers, patterned wafers, sawn wafers, and wafers of any kind on film frames, dies, die in gel paks, die in waffle paks, multi-chip modules often called MCMs, JEDEC trays, Auer boats, and other wafer and die package configurations for defects, the method comprising:

determining an upper and a lower limit for each pixel on a substrate divided into a grid of pixels, the upper and lower limits for each pixel being calculated as a relationship of a color measurement for that pixel on a plurality of substrates known as good quality substrates, and specifically as the upper limit is a maximum of one of a mean of the color measurement for a given pixel plus a product of a standard deviation of the color measurement for the given pixel multiplied by a first sensitivity, or the mean for the given pixel plus a first minimum contrast for the given pixel, and the lower limit is a minimum of one of the mean of the color measurement for a given pixel plus a product of the standard deviation of the color measurement for the given pixel multiplied by a second sensitivity, or the mean for the given pixel plus a second minimum contrast for the given pixel;

comparing a color measurement for each pixel from an unknown quality substrate with the upper and lower limit for that pixel; and categorizing each compared pixel as either good if its color measurement is between the upper and lower limit, or bad if its color measurement is outside of the upper and lower limit.

17. An automated method of inspecting a substrate such as a wafer in any form including bare wafers, whole wafers, patterned wafers, sawn wafers, and wafers of any kind on film frames, dies, die in gel paks, die in waffle paks, multi-chip modules often called MCMs, JEDEC trays, Auer boats, and other wafer and die package configurations for defects, the method comprising:

determining a gray scale measurement for each pixel in a plurality of pixels on a known good quality substrate;

repeating the determining a gray scale measurement step for a plurality of known good quality substrates;

determining an upper and a lower limit from the gray scale measurements for each pixel, the upper limit being determined by calculating a maximum of one of a mean of the gray scale measurement for a given pixel plus a product of a standard deviation of the gray scale measurement for the given pixel multiplied by a first sensitivity, or the mean for the given pixel plus a first minimum contrast for the given pixel, and the lower limit being determined by calculating a minimum of one of the mean of the gray scale measurement for a given pixel plus a product of the standard deviation of the gray scale measurement for the given pixel multiplied by a second sensitivity, or the mean for the given pixel plus a second minimum contrast for the given pixel;

comparing each pixel from an unknown quality substrate with the upper and lower limit for that given pixel location; and categorizing each compared pixel as either good if its gray scale measurement is between the upper and lower limit, or bad if its gray scale measurement is outside of the upper and lower limit.

18. An automated system for inspecting a substrate such as a wafer in any form including whole patterned wafers, sawn wafers, broken wafers, and wafers of any kind on film frames, dies, die in gel paks, die in waffle paks, multi-chip modules often called MCMs, JEDEC trays, Auer boats, and other wafer and die package configurations for defects, the system comprising:

a wafer test plate;

means for providing a wafer to the test plate;

a wafer alignment device for aligning each and every wafer provided to the test plate at the same x, y, z, and θ location;

a visual inspection device for visual inputting of a plurality of known good quality wafers during training and for visual Inspection of other unknown quality wafers during inspection, a microprocessor having processing and memory capabilities for developing a model of a good quality wafer by taking a gray scale measurement for each said pixel on a plurality of known good quality wafers and determining an upper and a lower limit for each pixel from the plurality of known good quality wafers, the upper limit being a maximum of one of a mean of the gray scale measurement for a given pixel plus a product of a standard deviation of the gray scale measurement for the given pixel multiplied by a first sensitivity, or the mean for the given pixel plus a first minimum contrast for the given pixel, and the lower limit being a minimum of one of the mean of the gray scale measurement for a given pixel plus a product of the standard deviation of the gray scale measurement for the given pixel multiplied by a second sensitivity, or the mean for the given pixel plus a second minimum contrast for the given pixel, and the microprocessor further comparing other unknown quality wafers in comparison to the model by determining a gray scale measurement for each pixel thereon and comparing it to the upper and lower limits.

19. The automated system of claim 18 further comprising a focusing mechanism for focusing an image of at least a portion of the wafer as seen by the camera.

20. The automated system of claim 18 where the visual inspection device is a camera.

21. The automated system of claim 18 where the visual inspection device is a CCD camera.

22. The automated system of claim 18 further comprising a parameter input device for inputting parameters and other constraints or information including sensitivity parameters, geometries, die size, die shape, die pitch, number of rows, and number of columns.

23. The automated system of claim 18 further comprising a display for displaying the view being seen by the visual inspection device at present or at any previous saved period.

24. The automated system of claim 18 further including a marking head for placing a mark on or adjacent a pixel on a wafer that is outside of the model.

25. The automated system of claim 18 further including a frame on which the wafer test plate, the wafer alignment device, the visual inspection device, and the computer system are attached, and a hood for enclosing an inspection area over the test plate.

26. An automated system for inspecting a substrate such as a wafer in any form including bare wafers, whole wafers, patterned wafers, sawn wafers, and wafers of any kind on film frames, dies, die in gel paks, die in waffle paks, multi-chip modules often called MCMs, JEDEC trays, Auer boats, and other wafer and die package configurations for defects, the system comprising:

a wafer test plate;

means for providing a wafer to the test plate;

a wafer alignment device for aligning each and every wafer provided to the test plate at the same x, y, z, and θ location;

a visual inspection device for visual inputting of a plurality of known good quality wafers during training and for visual inspection of other unknown quality wafers during inspection, a microprocessor having processing and memory capabilities for developing a model of a good quality wafer by taking a visually perceived contrast for each said pixel on a plurality of known good quality wafers and determining an upper and a lower limit for each pixel from the plurality of known good quality wafers, the upper limit being a maximum of one of a mean of the visually perceived contrast for a given pixel plus a product of a standard deviation of the visually perceived contrast for the given pixel multiplied by a first sensitivity, or the mean for the given pixel plus a first minimum contrast for the given pixel, and the lower limit being a minimum of one of the mean of the visually perceived contrast for a given pixel plus a product of the standard deviation of the visually perceived contrast for the given pixel multiplied by a second sensitivity, or the mean for the given pixel plus a second minimum contrast for the given pixel, and the microprocessor further comparing other unknown quality wafers in comparison to the model by determining a visually perceived contrast for each pixel thereon and comparing it to the upper and lower limits.

* * * * *